(12) United States Patent
Olle

(10) Patent No.: US 8,491,893 B2
(45) Date of Patent: Jul. 23, 2013

(54) ONCOFETAL ANTIGEN/IMMATURE LAMININ RECEPTOR ANTIBODIES FOR DIAGNOSTIC AND CLINICAL APPLICATIONS

(75) Inventor: Eric W. Olle, Unicoi, TN (US)

(73) Assignee: Quantum Immunologics, Inc., Tampa, FL (US)

( * ) Notice: Subject to any disclaimer, the term of this patent is extended or adjusted under 35 U.S.C. 154(b) by 426 days.

(21) Appl. No.: 12/732,880

(22) Filed: Mar. 26, 2010

(65) Prior Publication Data

US 2010/0247536 A1    Sep. 30, 2010

Related U.S. Application Data

(60) Provisional application No. 61/163,810, filed on Mar. 26, 2009.

(51) Int. Cl.
*A61K 39/395*    (2006.01)
*C07K 16/28*    (2006.01)

(52) U.S. Cl.
USPC .................. 424/130.1; 424/141.1; 530/387.1; 530/388.1

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 6,331,415 | B1 | 12/2001 | Cabilly et al. |
| 2005/0244899 | A1 | 11/2005 | Young et al. |
| 2006/0165709 | A1 | 7/2006 | Coggin et al. |
| 2009/0068234 | A1 | 3/2009 | Biragyn et al. |

OTHER PUBLICATIONS

Castronovo et al., Immunodetection of the metastasis-associated laminin receptor in human breast cancer cells obtained by fine-needle aspiration biopsy. Am J Pathol. Dec. 1990;137(6):1373-1381.*
Wewer et al., Altered levels of laminin receptor mRNA in various human carcinoma cells that have different abilities to bind laminin. Proc Natl Acad Sci U S A. Oct. 1986;83(19):7137-7141.*
Viacava et al., The Spectrum of 67-kD Laminin Receptor Expression in Breat Carcinoma Progression, J. Pathol. 182 (1997) pp. 36-44.
Weissman et al., Three populations of cells with dendritic morphology exist in peripheral blood, only one of which is infectable with human immunodeficiency virus type 1, Proc. Nat'l. Acad. Sci. U.S.A. 92:3 (1995) pp. 826-830.
Wewer et al., Altered levels of laminin receptor mRNA in various human carcinoma cells that have different abilities to bind laminin, Proc. Nat'l. Acad. Sci. 83 (1986) pp. 7137-7141.
Zelle-Rieser et al., Expression and Immunogenicity of Oncofetal Antigen-Immature Laminin Receptor in Human Renal Cell Carcinoma, J. Urol. 165 (2001) pp. 1705-1709.
Zhou et al., A distinct pattern of cytokine gene expression by human CD83+ blood dendritic cells, Blood 86:9 (1995) pp. 3295-3301.
Zhou et al., CD14+ blood monocytes can differentiate into functionally mature CD83+ dendritic cells, Proc. Nat'l Acad. Sci. 93:6 (1996) pp. 2588-2592.
Zhou et al., Human blood dendritic cells selectively express CD83, a member of the immunoglobulin superfamily, J. Immunol 154:8 (1995) pp. 3821-3835.
Zola, Monoclonal Antibodies: A Manual of Techniques, CRC Press, Inc. (1987) pp. 147-158.
Ardini et al., Co-regulation and Physical Association of the 67-kDa Monomeric Laminin Receptor and the a6b4 Integrin, J. Biol. Chem. 272:4 (1997) pp. 2342-2345.
Barsoum et al., Immunogenicity of a Soluble Partially Purified Oncofetal Antigen from Murine Fibrosarcoma in Syngeneic Mice, J. Biol. Resp. Mod. 8 (1989) pp. 579-592.
Barsoum et al., Isolation and Partial Characterization of a Soluble Oncofetal Antigen from Murine and Human Amniotic Fluids, Int. J. Cancer 48 (1991) pp. 248-252.
Biragyn et al., Tumor-Associated Embryonic Antigen-Expressing Vaccines that Target CCR6 Elicit Potent CD8+ T Cell-Mediated Protective and Therapeutic Antitumor Immunity, J. Immunol. 179:2 (2007).
Castronovo et al., Functional Domains of the 67-kDa Laminin Receptor Precursor, J. Biol. Chem. 266:30 (1991) pp. 20440-20446.
Castronovo et al., Immunodetection of the Metastasis-associated Laminin Receptor in Human Breast Cancer Cells Obtained by Fine-needle Aspiration Biopsy, Am. J. Pathol. 137:6 (1990).
Coggin et al., 37 KiloDalton Oncofetal Antigen Protein and Immature Laminin Receptor Protein are Identical, Universal T-Cell Inducing Immunogens on Primary Rodent and Human Cancers, Anticancer Res. 19 (1999) pp. 5535-5542.
Coggin, Jr. et al., 44-kd Oncofetal Transplantation Antigen in Rodent and Human Fetal Cells, Head Neck Surg. 119 (1993).
Coggin, Jr. et al., A new immunobiological view of radiation-promoted lymphomagenesis, Int. J. Radiat. Biol. 71:1 (1997) pp. 81-94.
Coggin, Jr. et al., Radiation-Induced Lymphoblastic Lymphomas/Leukemias and Sarcomas of Mice Express Conserved, Immunogenic 44-Kilodalton Oncofetal Antigen, Am. J. Pathol. 130:1 (1988).
Coggin, Jr. et al., True Immunogenicity of Oncofetal Antigen/Immature Laminin Receptor Protein, Cancer Res. 64 (2004).
Davis et al., Identification and Partial Characterization of Laminin Binding Proteisns in Immature Rat Sertoli Cells, Experimental Cell Res. 193 (1991) pp. 262-273.
Donnes et al., Prediction of MHC class I bonding peptides, using SVMHC, BMC Bioinformatics 3:1 (2002) p. 25.
European Examination Report for Application No. EP10712235.0 dated Jul. 12, 2012.
Freudenthal et al., The distinct surface of human blood dendritic cells, as observed after an improved isolation method, Proc. Nat'l Acad. Sci. U.S.A. 87:19 (1990) pp. 7698-7702.

(Continued)

*Primary Examiner* — Ruixiang Li
(74) *Attorney, Agent, or Firm* — Lerner, David, Littenberg, Krumholz & Mentlik, LLP

(57) ABSTRACT

The present invention relates to antibodies against Oncofetal Antigen/immature Laminin receptor protein (OFA/iLRP) that can be used singly or in conjunction to detect or treat OFA/iLRP-related diseases. More specifically, the antibodies can be used for several purposes including: (i) detecting and measuring OFA/iLRP in different biofluids; and (ii) using OFA/iLRP with an antibody directed against the monomeric form and its associated diseases.

19 Claims, 7 Drawing Sheets

OTHER PUBLICATIONS

Friedrichs et al., Humoral Immune Responses against the Immature Laminin Receptor Protein Show Prognostic Significance in Patients with Chronic Lymphocytic Leukemia, J. Immunol. 180:9 (2008).
Giannopoulos et al., Targets and strategies for T-cell based vaccines in patients with B-cell chronic lymphocytic leukemia, Leuk. & Lymph. 47:10 (2006) pp. 2028-2036.
Gussack et al., Human Squamous Cell Carcinoma Lines Express Oncofetal 44-kD Polypeptide Defined by Monoclonal Antibody to Mouse Fetus, Cancer 62:2 (1988).
Höltl et al., Immunotherapy of Metastatic Renal Cell Carcinoma with Tumor Lysate-pulsed Autologous Dendritic Cells, Clin. Cancer Res. 8 (2002) pp. 3369-3376.
International Search Report for Application No. PCT/US2010/028945 dated Aug. 24, 2010.
International Search Report for Application No. PCT/US2010/028948 dated Aug. 24, 2010.
Jackers et al., Isolation from a multigene family of the active human gene of the metastasis-associated multifuncational protein 37LRP/p40 at chromosome 3p21.3, Oncogene 13 (1996) pp. 495-503.
Jamieson et al., Crystal Structure of the Human Laminin Receptor Precursor, J. Biol. Chem. 283:6 (2008) pp. 3002-3005.
Karpatová et al., Shedding of the 67-kD Laminin Receptor by Human Cancer Cells, J. Cellular Biochem. 60:226-234 (1996).
Kazmin et al., Phage display mapping for peptide 11 sensitive sequences binding to laminin-1, J. Molec. Biol. 298:3 (2000) pp. 431-445.
Ladner et al., Phage display-derived peptides as therapeutic alternatives to antibodies, Drug Discovery Today 9:12 (2004) pp. 525-529.
Lesot et al., Isolation of a laminin-binding protein from muscle cell membranes, EMBO J. 2:6 (1983) pp. 861-865.
Liotta et al., Monoclonal Antibodies to the Human Laminin Receptor Recognize Structurally Distinct Sites, Experimental Cell Res. 156 (1985) pp. 117-126.
Magnifico et al., Peptide G, Containing the Binding Site of the 67-kDa Laminin Receptor, Increases and Stabilizes Laminin Binding to Cancer Cells, J. Biol. Chem. 271:49 (1996) pp. 31179-31184.
Malinoff et al., Isolation of a Cell Surface Receptor Protein for Laminin from Murine Fibrosarcoma Cells, J. Cell Biol. 96 (1983) pp. 1475-1479.
McCafferty et al., Nature 348 (1990) pp. 552-554.
Muyldermanns, "Single domain camel antibodies: current status", Reviews in Molecular Biotechnology, 74 (2001) pp. 277-302.
Ménard et al., The 67 kDa laminin receptor as a prognostic factor in human cancer, Breat Cancer Res. & Treatment 52 (1998) pp. 137-145.
Payne, Jr. et al., Mouse Monoclonal Antibody to Embryonic Antigen: Development, Cross-Reactivity With Rodent and Human Tumors, and Preliminary Polypeptide Characterization, J. Nat'l Cancer Inst. 75:3 (1985).
Rammensee et al., SYFPEITHI: database for MHC ligands and peptide motifs, Immunogenetics 50:3-4 (1999) pp. 213-219.
Rao et al., Isolation of a Tumor Cell Laminin Receptor, Biochem. & Biophys. Res. Comm. 111:3 (1983) pp. 804-808.
Reche et al., Prediction of MHC class 1 binding peptides using profile motifs, Hum. Immunol. 63:9 (2002) pp. 701-709.
Rohrer et al., CD8 T cell clones inhibit antitumor T cell function by secreting IL-10, Immunol. 155:12 (1995) pp. 5719-5727.
Rohrer et al., Differential recognition of murine tumor-associated oncofetal transplantation antigen and individually specific tumor transplantation antigens by syngeneic cloned BALB/c and RDM mouse T cells, J. Immunol. 152:2 (1994) pp. 754-764.
Rohrer et al., Expression of 44-Kilodalton Oncofetal Antigen as a Premalignancy Marker in X Irradiation-Induced Murine T-Cell Lymphoma, J Nat'l Cancer Inst 84:8 (1992) pp. 602-609.
Rohrer et al., Human Breast Carcinoma Patients Develop Clonable Oncofetal Antigen-Specific Effector and Regulatory T Lymphocytes, J. Immunol. (1999).
Rohrer et al., Identification of oncofetal antigen/immature laminin receptor protein epitopes that activate BALB/c mouse OFA/LRP-specific effector and regulatory T cell clones, J. Immunol. 176:5 (2006) pp. 2844-2856.
Sakamoto et al., Inhibition of Angiogenesis and Tumor Growth by a Synthetic Laminin Peptide CSPGYIGSR-NH-2, Cancer Res. 51:3 (1991) pp. 903-906.
Sanjuán et al., Overexpression of the 67-kD Laminin Receptor Correlates with Tumour Progression in Human Colorectal Carcinoma, J. Pathol. 179 (1996) pp. 376-380.
Siegel et al., Identification of HLAa-A*0201-Presented T Cell Epitopes Derived from the Oncofetal Antigen-Immature Laminin Receptor Protein in Patients with Hematological Malignancies, J. Immun. (2006), vol. 176 No. 11, pp. 6935-6944 XP002571022.
Siegel et al., In-vivo detectable antibodies directed against the oncofetal antigen/immature laminin receptor can recognize and control myeloma cells—clinical implications, Leuk. 22 (2008) pp. 2115-2118.
Siegel et al., Induction of cytotoxic T-cell responses agianst the oncofetal antigen-immature laminin receptor for the treatment of hematologic malignancies, Blood 102:13 (2003).
Snider, Jr., The tuberculin skin test, Am. Rev. Respir. Dis. 125 (1982) pp. 108-118.
Taraboletti et al., Enhancement of Metastatic Potential of Murine and Human Melanoma Cells by Laminin Receptor Peptide G: Attachment of Cancer Cells to Subendothelial Matrix as a Pathway for Hematogenous Metastasis, J. Nat'l Cancer Inst. 85:3 (1993).
Thomas et al., Human peripheral blood dendritic cell subsets, isolation and characterization of precursor and mature antigen-presenting cells, J. Immunol. 153:9 (1994) pp. 4016-4028.

* cited by examiner

A.

B.

SEQUENCE LISTING

```
<160> NUMBER OF SEQ ID NOS: 40

<210> SEQ ID NO 1
<211> LENGTH: 15
<212> TYPE: PRT
<213> ORGANISM: Artificial Sequence
<220> FEATURE:
<223> OTHER INFORMATION: laminin receptor epitope

<400> SEQUENCE: 1

Thr Glu Asp Trp Ser Ala Gln Pro Ala Thr Glu Asp Trp Ser Ala
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: immunogenic region of oncofetal
      antigen/immature laminin receptor protein

<400> SEQUENCE: 2

Phe Phe Arg Glu Pro Arg Leu Leu Val Val Thr Asp Pro Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: immunogenic region of oncofetal
      antigen/immature laminin receptor protein

<400> SEQUENCE: 3

Val Thr Asp Pro Arg Ala Asp His Gln Pro Leu Thr Glu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: immunogenic region of oncofetal
      antigen/immature laminin receptor protein
```

```
<400> SEQUENCE: 4

Tyr Arg Asp Pro Glu Glu Ile Glu Lys Glu Glu Gln
1               5                   10

<210> SEQ ID NO 5
<211> LENGTH: 14
<212> TYPE: PRT
<213> ORGANISM: Artificial Sequence
<220> FEATURE:
<223> OTHER INFORMATION: immunogenic region of oncofetal
      antigen/immature laminin receptor protein

<400> SEQUENCE: 5

Phe Pro Thr Glu Asp Trp Ser Ala Gln Pro Ala Thr Glu Asp
1               5                   10

<210> SEQ ID NO 6
<211> LENGTH: 13
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 6

Phe Arg Glu Pro Arg Leu Leu Val Val Thr Asp Pro Arg
1               5                   10

<210> SEQ ID NO 7
<211> LENGTH: 19
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 7

Phe Arg Glu Pro Arg Leu Leu Val Val Thr Asp Arg Ala Asp His Gln
1               5                   10                  15

Pro Leu Thr

<210> SEQ ID NO 8
<211> LENGTH: 14
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 8

Phe Arg Glu Pro Arg Leu Leu Val Val Thr Asp Pro Arg Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: immunizing peptide designed against OFA/iLRP
      antibodies

<400> SEQUENCE: 9

Tyr Arg Asp Pro Glu Glu Ile Glu Lys Glu Glu Gln Cys
1               5                   10
```

```
<210> SEQ ID NO 10
<211> LENGTH: 7
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 10

Ala Leu Asp Val Leu Gln Met
1               5

<210> SEQ ID NO 11
<211> LENGTH: 10
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 11

Asp Val Leu Lys Phe Leu Ala Ala Gly Thr
1               5                   10

<210> SEQ ID NO 12
<211> LENGTH: 6
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 12

Glu Gln Tyr Ile Tyr Lys
1               5

<210> SEQ ID NO 13
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 13

Phe Arg Glu Pro Arg Leu Leu Val Val Thr Asp Pro Arg Ala Asp His
1               5                   10                  15

Gln Pro Leu Thr
            20

<210> SEQ ID NO 14
<211> LENGTH: 7
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 14

Gly Ile Tyr Ile Ile Asn Leu
1               5

<210> SEQ ID NO 15
<211> LENGTH: 22
<212> TYPE: PRT
<213> ORGANISM: Artificial Sequence
<220> FEATURE:
<223> OTHER INFORMATION: region of the oncofetal antigen/immature
      laminin receptor protein
```

-continued

<400> SEQUENCE: 15

Asp His Gln Pro Leu Thr Glu Ala Ser Tyr Val Asn Leu Pro Thr Ile
1               5                   10                  15

Ala Leu Cys Asn Thr Asp
            20

<210> SEQ ID NO 16
<211> LENGTH: 13
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 16

Lys Leu Leu Leu Ala Ala Arg Ala Ile Val Ala Ile Glu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 17

Gly Val Gln Val Pro Ser Val Pro Ile Gln Gln Phe
1               5                   10

<210> SEQ ID NO 18
<211> LENGTH: 9
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 18

Pro Ala Asp Val Ser Val Ile Ser Ser
1               5

<210> SEQ ID NO 19
<211> LENGTH: 7
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 19

Ala Thr Pro Ile Ala Gly Arg
1               5

<210> SEQ ID NO 20
<211> LENGTH: 11
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 20

Pro Leu Arg Tyr Val Asp Ile Ala Ile Pro Cys
1               5                   10

-continued

```
<210> SEQ ID NO 21
<211> LENGTH: 6
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 21

Ala His Ser Val Gly Leu
1               5

<210> SEQ ID NO 22
<211> LENGTH: 12
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 22

Val Val Thr Asp Arg Ala Asp His Gln Pro Leu Thr
1               5                   10

<210> SEQ ID NO 23
<211> LENGTH: 8
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 23

Met Pro Asp Leu Tyr Phe Tyr Arg
1               5

<210> SEQ ID NO 24
<211> LENGTH: 11
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 24

Val Val Thr Asp Pro Arg Ala Asp His Gln Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 25

Ala Pro Glu Phe Thr Ala Ala Gln Pro Glu Val Ala
1               5                   10

<210> SEQ ID NO 26
<211> LENGTH: 14
<212> TYPE: PRT
<213> ORGANISM: Artificial Sequence
<220> FEATURE:
<223> OTHER INFORMATION: immunizing peptide designed against OFA/iLRP
      antibodies
```

-continued

```
<400> SEQUENCE: 26

Cys Val Thr Asp Pro Arg Ala Asp His Gln Pro Leu Thr Glu
1               5                   10

<210> SEQ ID NO 27
<211> LENGTH: 15
<212> TYPE: PRT
<213> ORGANISM: Artificial Sequence
<220> FEATURE:
<223> OTHER INFORMATION: immunizing peptide designed against OFA/iLRP
      antibodies

<400> SEQUENCE: 27

Cys Phe Pro Thr Glu Asp Trp Ser Ala Gln Pro Ala Thr Glu Asp
1               5                   10                  15

<210> SEQ ID NO 28
<211> LENGTH: 6
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 28

Thr Glu Asp Trp Ser Ala
1               5

<210> SEQ ID NO 29
<211> LENGTH: 19
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 29

Thr Pro Gly Thr Phe Asn Gln Ile Gln Ala Ala Phe Arg Glu Pro Arg
1               5                   10                  15

Leu Leu Val

<210> SEQ ID NO 30
<211> LENGTH: 8
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 30

Ser Gly Ala Leu Asp Val Leu Gln
1               5

<210> SEQ ID NO 31
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 31

Ala Ala Gly Thr His Leu Gly Gly Thr Asn Leu Asp Phe Gln Met Glu
1               5                   10                  15

Gln Tyr Ile Tyr
            20
```

```
<210> SEQ ID NO 32
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 32

Asp Gly Ile Tyr Ile Ile Asn Leu Lys Arg Thr Trp Glu Lys Leu Leu
1               5                   10                  15

Leu Ala Ala Arg
            20

<210> SEQ ID NO 33
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 33

Ala Ile Val Ala Ile Glu Asn Pro Ala Asp Val Ser Val Ile Ser Ser
1               5                   10                  15

Arg Asn Thr Gly
            20

<210> SEQ ID NO 34
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 34

Gln Arg Ala Val Leu Lys Phe Ala Ala Ala Thr Gly Ala Thr Pro Ile
1               5                   10                  15

Ala Gly Arg Phe
            20

<210> SEQ ID NO 35
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 35

Thr Pro Gly Thr Phe Thr Asn Gln Ile Gln Ala Ala Phe Arg Glu Pro
1               5                   10                  15

Arg Leu Leu Val
            20

<210> SEQ ID NO 36
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein
```

```
<400> SEQUENCE: 36

Ala Leu Cys Asn Thr Asp Ser Pro Leu Ala Tyr Val Asp Ile Ala Ile
1               5                   10                  15

Pro Cys Asn Asn
            20

<210> SEQ ID NO 37
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 37

Ile Pro Cys Asn Asn Lys Gly Ala His Ser Val Gly Leu Met Trp Trp
1               5                   10                  15

Met Leu Ala Arg
            20

<210> SEQ ID NO 38
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 38

Ala Ala Ala Glu Lys Ala Val Thr Lys Glu Glu Phe Gln Gly Glu Trp
1               5                   10                  15

Thr Ala Pro Ala
            20

<210> SEQ ID NO 39
<211> LENGTH: 20
<212> TYPE: PRT
<213> ORGANISM: Artificial Sequence
<220> FEATURE:
<223> OTHER INFORMATION: region of the oncofetal antigen/immature
      laminin receptor protein

<400> SEQUENCE: 39

Gln Phe Pro Thr Glu Asp Trp Ser Ala Gln Pro Ala Thr Glu Asp Trp
1               5                   10                  15

Ser Ala Ala Pro
            20

<210> SEQ ID NO 40
<211> LENGTH: 15
<212> TYPE: PRT
<213> ORGANISM: Artificial Sequence
<220> FEATURE:
<223> OTHER INFORMATION: immunizing peptide designed against OFA/iLRP
      antibodies

<400> SEQUENCE: 40

Phe Phe Arg Glu Pro Arg Leu Leu Val Val Thr Asp Pro Arg Cys
1               5                   10                  15
```

ONCOFETAL ANTIGEN/IMMATURE LAMININ RECEPTOR ANTIBODIES FOR DIAGNOSTIC AND CLINICAL APPLICATIONS

The present application claims the benefit of the filing date of U.S. Provisional Application No. 61/163,810 filed Mar. 26, 2009, the disclosure of which is incorporated herein by reference in its entirety.

FIELD OF THE INVENTION

The present invention relates in general to the oncofetal antigen/immature laminin receptor protein (OFA/iLRP). More specifically, the invention provides antibodies that can be used to detect and treat OFA/iLRP-related diseases.

BACKGROUND OF THE INVENTION

The initial characterization of oncofetal antigen/immature laminin receptor protein (OFA/iLRP) was done by three independent groups, which studied oncofetal antigen or laminin receptor [1-3]. OFA/iLRP is a highly conserved protein that is over-expressed in a range of different cancers and has a dual function as ribosomal protein p40 [4-27]. The OFA/iLRP protein is comprised of a single polypeptide chain of 295 amino acids and has a molecular weight of about 37-44 kDa. The structure of OFA/iLRP has recently been elucidated to 2.15 Å [28]. The mature form of the laminin receptor (LRP) appears to be a dimer of acetylated OFA/iLRP, with a molecular weight of 67 kDa. The structure showed that the region between amino acids 112 to 140 of OFA/iLRP is involved in dimerization [28] of OFA/iLRP for forming the LRP. Although the 67 kDa LRP is on many normal cells as well as on tumor cells, there appears to be a preferential expression of the OFA/iLRP by fetal and tumor cells. Thus, the expression pattern makes OFA/iLRP a possible candidate protein to sensitize the immune system for the treatment of cancer and other diseases [6]. Antibodies specific for OFA/iLRP may also be used for the detection, diagnosis, and treatment of diseases known to be related to OFA/iLRP mis-expression.

The initial work on OFA/iLRP antibodies falls under two separate fields, the oncofetal antigen or the laminin receptor sides. The initial report of monoclonal antibodies against OFA/iLRP was found the same year for both the embryonic/fetal antigen and the laminin receptor [29, 30]. The antibodies developed against embryonic or fetal antigen reacted with a 44 kDa protein under denaturing conditions [30]. Antibodies previously developed against the laminin receptor had different biological activities based on the location of antibody binding [29]. One region that had biological activity of blocking laminin binding was recognized by monoclonal IgM antibody. The epitope that the monoclonal IgM antibody recognized was TEDWSAQPATEDWSA (SEQ. ID. NO.: 1) [26]. Studies on the 44 kDa OFA showed that the IgM monoclonal antibody (MAb 115) can be used for western blots, flow cytometry, and possibly oncogenicity testing [31]. However, since this antibody was not designed specifically against the OFA|OFA dimerization region, it reacts with both OFA/iLRP and LRP [31]. This monoclonal antibody was used for immunohistochemistry and protein purification of the OFA/iLRP or LRP [12, 32]. A different antibody was developed from peptides that detected the 67 kDa laminin receptor and showed increased laminin receptor expression in breast cancer [5,33]. Several published manuscripts describe the use of OFA/iLRP antibodies, while looking for autoimmune antibodies [6, 9, 10, 16, 19, 20, 25, 27, 34-36].

Since OFA/iLRP is associated with a range of different diseases, there is a need to develop diagnostic and clinical antibody applications. To date, there have been only a few attempts to develop a targeted antibody using peptides and this has been limited to one published report [5]. The region used in the published report produced antibodies that was reported to react with both the OFA/iLRP and laminin receptor [5,25]. Thus, a need exists to develop antibodies that are specific to OFA/iLRP, which can be used alone or in conjunction with other antibodies, to develop a range of different clinical, diagnostic, and/or veterinary applications. The development of antibodies in pairs, one that can recognize OFA/iLRP and one that can recognize both OFA/iLRP and LRP, allows for the development of several tests that can be use to treat, diagnosis or act as a reagent in OFA/iLRP diseases in all species due to the conserved nature of the protein.

SUMMARY OF THE INVENTION

One aspect of the present invention provides an isolated antibody that specifically binds to a region of the oncofetal antigen/immature laminin receptor protein (OFA/iLRP), wherein the region is immunogenic. In one embodiment, the immunogenic regions of OFA/iLRP include, but are not limited to, polypeptide sequences of (a) FFREPRLLVVTDPR (SEQ. ID. NO.: 2), (b) VTDPRADHQPLTE (SEQ. ID. NO.: 3), (c) YRDPEEIEKEEQ (SEQ. ID. NO.: 4), or (d) FPTEDWSAQPATED (SEQ. ID. NO.: 5). In another embodiment, the isolated antibody of the present invention is a polyclonal or monoclonal antibody, including but not limited to, monoclonal antibody 2C6 or 3G7. In further another embodiment, the immunogenic region is located in the dimerization region of OFA/iLRP.

The antibodies of the present invention are produced by immunizing against immunogenic regions of OFA/iLRP. The antibodies can recognize both the full-length OFA/iLRP protein and the immunogenic regions of OFA/iLRP that are used to produce the antibodies of the present invention. In one embodiment, the antibodies are specific for OFA/iLRP. In an alternative embodiment, the antibodies recognize both OFA/iLRP and mature LRP.

The antibodies of the invention can be used in different methods for detecting proteins or cancers related to OFA/iLRP.

In one embodiment, the antibodies are used in a method for detecting OFA/iLRP in a sample. The method comprises:
(a) contacting the sample with first and second antibodies that specifically bind to a region of the oncofetal antigen/immature laminin receptor protein (OFA/iLRP) respectively, wherein at least one of the antibodies is specific for OFA/iLRP;
(b) allowing the antibodies to bind to OFA/iLRP and form a sandwich with OFA/iLRP; and
(c) detecting the expression of OFA/iLR in the sample using the antibody specific for OFA/iLRP.

In one embodiment, one of the antibodies may bind to both OFA/iLRP and mature LRP, and act as a capture antibody. Another antibody may be specific for OFA/iLRP and acts as a detection antibody.

In another embodiment, the antibodies of the invention are used in a method of detecting cancer in a sample. The method comprises:
(a) contacting the sample with antibodies specific for OFA/iLRP;
(b) contacting the sample with a biotinylated secondary antibody; and
(c) detecting OFA/iLRP in the sample using streptavidin, wherein the detection of OFA/iLRP in the sample is indicative of cancer.

In a further embodiment, the invention provides a method of determining the amount of OFA/iLRP in a sample comprising:
- (a) conjugating an antibody specific for OFA/iLRP to a fluorophore;
- (b) contacting the conjugated antibody in a sample; and
- (c) determining the amount of OFA/iLRP in the sample using fluorescent polarization.

Antibodies of the present invention may also be used in a method of determining the amount of OFA/iLRP positive cancer cells in a blood sample. The method comprises:
- (a) contacting a blood sample with an antibody specific for OFA/iLRP and
- (b) determining the amount of OFA/iLRP in the sample using flow cytometry.

Antibodies of the invention may also be used in a method of treating a OFA/iLRP positive cancer. The method comprises administering an amount of antibodies specific for OFA/iLRP to a subject with the OFA/iLRP positive cancer that is sufficient to ameliorate the cancer-related symptoms. In one embodiment, the antibodies are linked to colloids having anti-cancer properties or are conjugated with chemotherapeutic agents or protein.

The present invention also provides methods of detecting a OFA/iLRP positive cancer in a subject. The method comprises:
- (a) conjugating antibodies specific for OFA/iLRP to a radiopaque dye;
- (b) administering the conjugated antibody to a subject; and
- (c) detecting the conjugated antibody using an x-ray, wherein the detection of OFA/iLRP on the x-ray is indicative of cancer.

Another aspect of the present invention provides a pharmaceutical composition comprising an antibody of the present invention. The composition may include a pharmaceutical carrier.

The above-mentioned and other features of this invention, and the manner of obtaining and using them, will become more apparent, and will be best understood by reference to the following description, taken in conjunction with the accompanying drawings. The drawings depict only typical embodiments of the invention and do not therefore limit its scope.

DETAILED DESCRIPTION OF THE INVENTION

Figure 1:
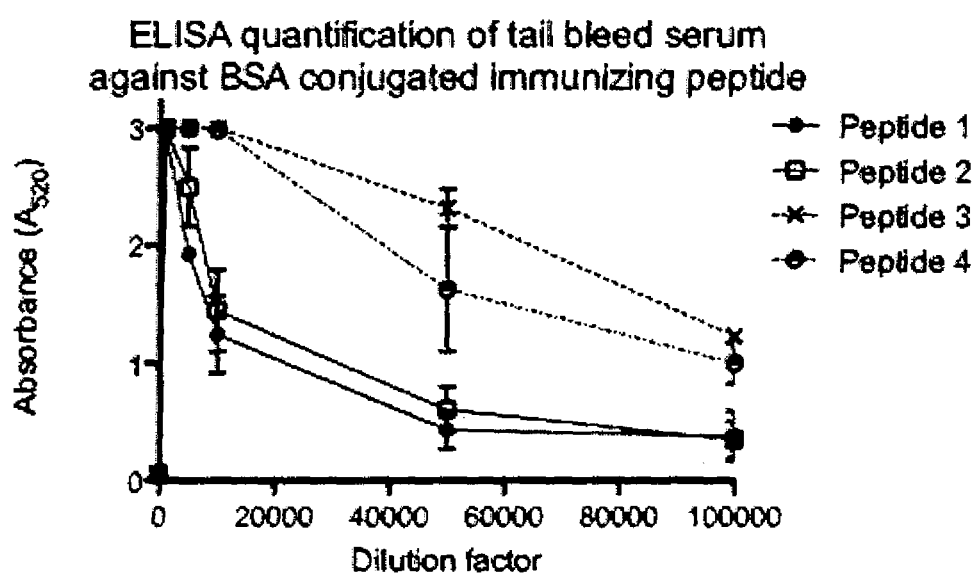
FIG. 1. Titration of OFA/iLRP polyclonal serum against BSA conjugate OFA/iLRP peptides. Detection of antibody antigen reaction used a biotinylated universal secondary antibody mixture. Absorbance was measured on a SpectraMax and data was analyzed using Prism Graph.

It was a surprise discovery of the present invention that immunogenic peptides may be derived from putative isotope regions of OFA/iLRP, and used to generate antibodies against specific regions of OFA/iLRP that were not previously discovered.

Accordingly, one aspect of the present invention is directed to an isolated antibody which specifically binds to a region of the oncofetal antigen/immature laminin receptor protein (OFA/iLRP), wherein the region is immunogenic. For the purpose of the present invention, an "isolated" antibody is one which has been identified and separated, and/or recovered from a component of its natural environment.

In one embodiment of the present invention, the antibody is specific for OFA/iLRP. An antibody is specific for OFA/iLRP if it preferentially binds to OFA/iLRP, not the 67 kDa form of the laminin receptor under a well-known standard antibody-binding condition. Examples of such an antibody include, but are not limited to, 3G7. In a different embodiment, the antibody of the present invention may recognize both OFA/iLRP and the 67 kDa form of the laminin receptor. Examples of such an antibody include, but are not limited to, 2C6. In a further embodiment, the antibody of the invention bind to the dimerization region of OFA/iLRP. For the purpose of the present invention, the dimerization region is a region between amino acids 112 to 140 of OFA/iLRP full-length protein that are involved in dimerization [28] of OFA/iLRP.

The antibodies of the present invention can recognize full length OFA/iLRP proteins. They can also recognize specific regions of OFA/iLRP that are immunogenic, particularly the dimerization region. For the purpose of the present invention, a region of OFA/iLRP is immunogenic if polypeptides derived from that region can provoke an immune response and can be used to produce the antibodies of the present invention. For example, antibodies generated by the four immunogenic peptides listed in Table 2 can recognize the full-length OFA/iLRP protein, their respective immunogenic peptides, and the regions of OFA/iLRP comprising those peptides.

For the purpose of the present invention, an "antibody" is an immunoglobulin molecule capable of specific binding to a target, such as a receptor, carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibody of the present invention is further intended to include bispecific, multispecific, single-chain, and chimeric and humanized molecules having affinity for a polypeptide conferred by at least one OFA/iLRP region of the antibody. Antibodies of the present invention also include single domain antibodies which are either the variable domain of an antibody heavy chain or the variable domain of an antibody light chain. Methods of making domain antibodies comprising either the variable domain of an antibody heavy chain or the variable domain of an antibody light chain, containing three of the six naturally-occurring complementarity-determining regions from an antibody, are also known in the art. See, e.g., Muyldermans, *Rev. Mol. Biotechnol.*, 74:277-302, 2001.

In one embodiment, the antibodies developed against OFA/iLRP are monoclonal antibodies. Monoclonal antibodies, such as 2C6 and 3G7, can also recognize the full length OFA/iLRP protein, their respective immunogenic peptides, and the regions of OFA/iLRP comprising those peptides. However, monoclonal antibody 3G7 does not recognize the mature form of LRP (the dimer form), whereas monoclonal antibody 2C6 does. Although, high doses of 3G7 antibody may disrupt the OFA/iLRP dimer.

As used herein, the term "monoclonal antibody" refers to an antibody of substantially homogeneous antibodies, i.e., the individual antibodies comprising the population are identical except for possible naturally-occurring mutations that may be present in minor amounts. Monoclonal antibodies are generally highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

The antibodies of the present invention are produced by immunizing against peptides based on selected criteria. The selection of the peptides and the selection criteria are fully disclosed in the patent application entitled "Oncofetal Antigen/Immature Laminin Receptor Peptides For The Sensitization Of Dendritic Cells For Cancer Therapy" which is concurrently filed with the present application, the relevant content of which is fully incorporated herein. In general, a polypeptide or peptide comprising at least a part, i.e., the whole or a part, of the amino acid sequence of OFA/iLRP, may be used as an antigen as long as it can elicit specific antibody response wherein the antibodies so generated can recognize both the full length OFA/iLRP and the immunogenic peptides used therein. According to embodiments of the present invention, immunogenic peptides are generated based on different putative epitope regions of OFA/iLRP. In order to increase reproducibility and the chances of a multi-functional antibody against OFA/iLRP, either to be used alone or in conjunction with the antibody against the dimerization region of OFA/iLRP, preferably, antibodies are developed against the regions or epitopes listed in Table 1. In one embodiment, the following four peptides are used for generating antibodies of the present invention: 1) FREPRLLVVTDPR (SEQ. ID. NO.: 6), 2) VTDPRADHQPLTE (SEQ. ID. NO.: 3), 3) YRDPEEIEKEEQ (SEQ. ID. NO.: 4), 4) FPTEDWSAQPATED (SEQ. ID. NO.: 5).

The peptides of the present invention may be prepared by chemical synthesis or biochemical synthesis using *Escherichia coli* or the like. Methods well known to those skilled in the art may be used for the synthesis.

When the peptide of the invention is chemically synthesized, methods well known in the field of peptide synthesis may be used. For example, such methods as the azide method, the acid chloride method, the acid anhydride method, the mixed acid anhydride method, the DCC method, the active ester method, the carbodiimidazole method and the oxidation-reduction method may be enumerated. Either solid phase synthesis or liquid phase synthesis may be used. A commercial peptide synthesizer (e.g., Shimadzu PSSM-8) may also be used.

After the reaction, the peptide of the invention may be purified by a combination of conventional purification methods such as solvent extraction, distillation, column chromatography, liquid chromatography, or re-crystallization.

The peptides of the invention may be modified to increase its immunogenic response. In one embodiment, alterations of the peptides may include a cysteine residue at either end that allow for conjugation to Keyhole Limpet hemocyanin, ovalbumin, serum albumin, or other conjugates used to increase a peptide immunogenic response. Table 2 lists the examples of modified peptides for conjugation.

The peptides can be used in a range of different organisms to create antibodies. The antibodies can also be cloned to generate a range of different recombinant antibodies based on well-known protein technologies. One of the objectives of the present invention is to develop antibodies directed against specific regions of OFA/iLRP by immunizing against the peptides of the present invention instead of immunizing against the full-length protein, and selecting antibodies based on their immuno-specificities against specific regions of OFA/iLRP.

The monoclonal antibodies of the present invention can be generated using methods known in the art. For example, they may be generated by culturing the hybridoma cells, and the antibodies secreted by the hybridoma cells may further be isolated or purified. Antibodies may be isolated or purified from the culture medium or ascites fluid by conventional immunoglobulin purification procedures such as, for example, protein A-Sepharose®, hydroxylapatite chromatography, gel electrophoresis, dialysis, or affinity chromatography.

The antibodies of the invention can also be made by recombinant DNA methods, such as those described in U.S. Pat. Nos. 4,816,567 and 6,331,415, which are hereby incorporated by reference, for example, DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells, such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies of the present invention can be used for a range of different functions. In one embodiment, antibodies of the present invention may be used to detect malignant tissue through conjugation with chemical, radiological, and nuclear adjuvants. Additionally, these antibodies may be used as therapeutically to provide passive immunity, increased immune response in its native or altered or if conjugated to a: chemical, radiological "seed" source, microelectrical devices, silver colloid, gold, titanium dioxide colloid, biopolymer colloid (i.e., starch, collagen, agarose, etc.), peptide sequence or protein sequence, to aid in the targeted destruction of malignant cells. Due to the highly conserved nature of OFA/iLRP, the antibodies can also be used as a reagent and should cross-react with all organisms that express the protein. Accordingly, another aspect of the present invention provides pharmaceutical compositions comprising antibodies or polypeptides described herein. The antibodies or polypeptides of the compositions may be used alone or conjugated to chemical, radiological "seed" source, microelectrical devices, silver colloid, gold, titanium dioxide colloid, biopolymer colloid (i.e., starch, collagen, agarose, etc.), peptide sequence, or protein sequence, that can aid in the targeted destruction of malignant cells.

The compositions may also comprise a pharmaceutically acceptable carrier or excipients. Pharmaceutically acceptable excipients are known in the art, and are relatively inert substances that facilitate the administration of a pharmacologically-effective substance. For example, an excipient can give form or consistency, or act as a diluent. Suitable excipients include, but are not limited to, stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

The composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Compositions suitable for injectable use include sterile aqueous solutions (where water soluble) or dispersions, and sterile powders for the extemporaneous preparation of sterile injectable solutions or dispersion. For intravenous administration, suitable carriers include physiological saline, sterile water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage, and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the compounds in the required amounts in an appropriate solvent with one or a combination of ingredients enumerated above, as required, followed by filtered sterilization. Generally, dispersions are prepared by incorporating the compounds into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the compounds can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compositions are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compositions of the invention can also be prepared in the form of suppositories (e.g., with conventional suppository bases such as cocoa butter and other glycerides) or retention enemas for rectal delivery.

In one embodiment, the compositions are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers.

It is advantageous to formulate oral or parenteral compositions in dosage unit form for ease of administration and uniformity of dosage. "Dosage unit form," as used herein, refers to physically discrete units suited as unitary dosages for the subject to be treated. Each unit contains a predetermined quantity of active compound calculated to produce the desired therapeutical effect in association with the required pharmaceutical carrier.

The compositions of the invention can be included in a container, pack, or dispenser, together with instructions for administration to form packaged products. Other active compounds can also be incorporated into the compositions.

A further aspect of the present invention provides a method of using the antibodies and polypeptides of the present invention for detection, diagnosis, and monitoring of a disease, disorder, or condition associated with the epitope expression of OFA/iLRP, either increased or decreased relative to a normal sample, and/or inappropriate expression, such as the presence of expression in tissues(s) and/or cell(s) that normally lack the epitope expression.

In some embodiments, the method comprises detecting the epitope expression in a sample obtained from a subject suspected of having cancer, or any disease that is associated with OFA/iLRP. Preferably, the method of detection comprises contacting the sample with an antibody or polypeptide of the present invention under a condition that allows the binding of the antibody to the epitope region of OFA/iLRP and determining whether the level of binding differs from that of a control or comparison sample. The method is also useful to determine whether the antibodies or polypeptides described herein are an appropriate treatment for the patient.

For purposes of diagnosis, the polypeptide including antibodies can be labeled with a detectable moiety including, but not limited to, radioisotopes, fluorescent labels, and various enzyme-substrate labels known in the art. Methods of conjugating labels to an antibody are known in the art.

In some embodiments, the polypeptides including antibodies of the invention need not be labeled, and the presence thereof can be detected using a labeled antibody which binds to the antibodies of the invention.

The antibodies of the present invention can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, or $^{3}$H), so that the cells or tissue of interest can be localized using immunoscintigraphy.

The antibody may also be used as a staining reagent in pathology using techniques well known in the art.

The invention will be further described by reference to the following detailed embodiments and examples. These embodiments and examples are provided for the purposes of illustration only, and are not intended to limit the scope of the invention described herein.

Development of Antibodies Against Specific Regions of OFA/iLRP

Antibodies are made against OFA/iLRP using a range of different peptides that are directed against a range of different putative epitope regions of OFA/iLRP. Table 1 provides a list of such peptides. The peptides are conjugated to Keyhole Limpet Hemocyanin (KLH) following standard protocols [37-39]. The KLH-OFA/iLRP peptides are used to immunize mice following standard protocols [37, 39]. After the third immunization against the KLH-OFA/iLRP peptide, the serum isolated from mouse-tail bleed are screened against bovine serum albumin (BSA) conjugated-OFA/iLRP peptides using an indirect ELISA technique using standard protocols (FIG. 1 and Table 1). Briefly, OFA/iLRP was coated on a Nunc Star Immunosorp plate overnight at 4° C. The plate was washed and blocked 3 times with water. Mouse serum obtained via tail bleed was diluted in PBS-t with BSA and was incubated for 1 hour at room temp. The plate was washed and the antibody antigen interaction was detected using standard methods with a biotinylated secondary antibody (FIGS. 1A-B). Absorbance was read at A620 on a Beckman DTX 880 and graphed using Prism Graph 5 (FIG. 1C). The bars show the mean of two independent experiments from two animals per immunizing peptide. Positive control was coated with BSA and BSA antibodies. The negative control had no protein coating.

In addition to peptide screening, the tail-bleeds are tested against OFA/iLRP isolated using standard protocols [1-3, 5, 26, 29, 30]. Briefly, full length OFA/iLRP is coated on a Nunc-Immuno Star MaxiSorp plate and diluted to 5 µg/ml in PBS with sodium azide for 2 hours at 37° C. The plates are washed three times in 18.2 megaohm water and blocked for 1 hour at 25° C. using PBS-t with 5% dry milk powder. The plate is washed 3 times with PBS-t. The serum from the tail bleed is diluted in blocking buffer (above) and incubated overnight at 4° C. The plate is washed using PBS-t as above. The antibody-antigen complex is detected using a biotin goat anti-mouse antibody, diluted in blocking buffer, and incubated for 1 hour at 25° C. The plate is washed three times using PBS-t. The secondary antibody is detected using Strepavidin-Horseradish Peroxidase (HRP), diluted in the blocking buffer, and incubated for 30 min at 25° C. Plates are washed as above. The final detection step follows standard protocols using a Sigma FAST™ OPD system and read on a SpectraMax 384.

Antibodies Used In An Antibody-Sandwich ELISA To Detect OFA/iLRP

The expression of OFA/iLRP RNA and protein have been linked to more aggressive forms of cancer [2, 3, 5, 6, 8, 10, 13, 15-17, 20, 21, 23, 25, 26, 29, 40]. However, the protein work has primarily concentrated on the 67 kDa form and immunohistochemistry. One of the objects of the present invention is to develop a standard sandwich ELISA where two OFA/iLRP antibodies designed against distinct regions are used. The capture antibody that is specific for OFA/iLRP can be used to quantify the amount of 37 kDa OFA/iLRP present, and capture antibodies outside this region can be used to quantify total OFA/iLRP present.

Briefly, the antibody-sandwich ELISA follows standard techniques as follows. The capture antibody is coated on a Nunc Star Immunosorb plate (or similar) which is then coated with a range of different concentrations of capture antibody against the FREPRLLVVTDRADHQPLT (SEQ. ID. NO.: 7) peptide in carbonate buffer and incubated at 4° C. overnight. The optimum concentration of capture and detection antibody is determined using the "criss-cross" method of dilutions [39]. The plate is washed three times in water and three times with PBS-t. Once washed, the plate is blocked for 1 hour using a standard blocking buffer. The blocked plate is washed three times with PBS-t. The soluble protein lysate is tested with a standard blocking buffer and OFA/iLRP is incubated from 1 hour at room temperature to overnight at 4° C. When the initial incubation is completed, the plate is washed 3 times with PBS-t. To detect the OFA/iLRP capture antibody interaction, a secondary/detection antibody is diluted in blocking buffer and incubated at room temperature for at least one hour. The plate is washed 3 times using PBS-t. The detection antibody is conjugated to biotin (or other methods). The biotin conjugate is detected using Strepavidin/Horseradish Peroxidase (HRP) or the equivalent. The strepavidin is diluted in an appropriate block and incubated for 30 minutes at room temperature. The plate is washed and the HRP enzymatic conjugate on the strepavidin is detected using the SIGMA FAST™ OPD system following standard protocols. The amount of OFA/iLRP present is read on a SpectraMax 384 or the equivalent. The concentration of OFA/iLRP is back-calculated using the standard curve generated from purified OFA/iLRP and multiplied by the dilution factor following standard curve fitting methods [37]. It may also be possible to detect the monomeric form of OFA/iLRP by using a non-specific capture antibody, followed by using a detection antibody that is directed against the monomeric region. A combination of capture and detection antibodies against regions outside of the dimerization region can be used to determine the total amount of OFA/iLRP present in biofluids or tissue lysates.

To detect the native dimeric form of OFA/iLRP, a standard ELISA is used as above. However, instead of using an antibody developed against the monomeric region, the antibodies used are outside of this region, but have a great enough distance from the detection antibody used above to allow for proper binding. The 67 kDa OFA/iLRP is purified following standard protocols [2, 3, 26, 29]. The size is verified as above, either using native gel electrophoresis or size exclusion chromatography. A standard ELISA is performed with a capture antibody against an epitope that is different than FREPRLLVVTDRADHQPLT (SEQ. ID. NO.: 7) to capture the dimer, and then the biotinylated detection antibody used in the monomer detection is used. ELISA is processed following standard protocols [39]. This will determine the amount of dimer OFA/iLRP present in biofluids and tissue lysate. Additional information on the nature, metastatic load, and other clinically relevant information may be obtained by the ratio of monomeric OFA/iLRP to total OFA/iLRP.

Immunohistochemical Detection of OFA/iLRP

The antibodies listed above can be used for immunohistochemistry (IHC) as a method to detect cancer and possible cancer in situ. Similar techniques have been used to identify cancer, however, they detect the 67 kDa protein [5, 17, 41]. IHC methods follow the standard protocols that have been customized for OFA/iLRP detection. The protocol is similar to listed below:

Cut tissue is deparaffinized following standard protocols for histological analysis of tissue, such as xylenes, followed by descending concentrations of ethanol, and into at least Type I Lab water. Antigen retrieval follows standard protocol, using Heat Induced Epitope Retrieval (HIER) in 0.01 M citrate buffer adjusted to pH 6.0. The epitope(s) can be retrieved using either direct heat method (hotplate) or an indirect heat method (microwave) [37]. Briefly, the deparaffinized tissue sections are placed in a slide holder and placed in a staining dish filled with citrate buffer at >90° C. The tissue is heated and maintained >90° C. for around 10 minutes. The time of processing depends on the tissue type, tissue thickness, and a range of other factors. Once properly processed, the tissue is washed 3 times in phosphate buffered saline with 0.1% Tween-20 (PBS-t) following standard methods. The tissue is incubated with standard IHC blocking buffer (PBS-t with BSA or other reagents used to decrease non-specific antibody/protein interactions) at room temperature in a humid chamber. The slides are washed three times in PBS-t. The OFA/iLRP antibodies are diluted appropriately in PBS-t with BSA or the equivalent and incubated with the processed tissue. The slides are washed as above (3×PBS-t). The tissue is incubated with biotinylated universal secondary antibody (or equivalent) to allow for detection using a strepavidin-based system. The slides are washed as above and the OFA/iLRP|Ab|2° antibody complex is detected using standard strepavidin conjugated to either: Alkaline Phosphatase (AP), Horseradish Peroxidase (HRP), Quantum Dot, fluorophore, radio nucleotide, or other detection method [37, 39, 42]. The tissue is visualized following standard protocols.

Use of OFA/iLRP Antibodies For Fluorescent Polarization Quantification

The antibodies can be used for fluorescent polarization (FP) experiments to determine the amount of OFA/iLRP present. Additionally, a ratio of FP of monomer versus dimer may be possible. FP can also be used to determine the mobility of OFA/iLRP on the cell surface. Determining the use of the antibodies in a fluorescent polarization experiment is based upon previous work but is developed specifically for OFA/iLRP quantification [43-49]. In order to determine the use of OFA/iLRP antibodies, the monoclonal antibody is conjugated to a standard fluorophore and the labeled antibody can be removed from the free label following the SM-2 biobeads protocol [50]. Once purified, the protein concentration and fluorescent incorporation can be determined as a ratio of protein to fluorophore. Once conjugated, the antibody can be stored appropriately and used later.

To test the ability of the antibody to be used in FP experiments, the antibody can be mixed with the appropriate amounts similar to the determination of the antibody concentration commonly used for the ELISA technique [39]. Briefly, a 96-well plate designed for fluorescence is used having a double dilution with the amount of OFA/iLRP protein along one axis and the amount of labeled antibody along the other. The dilutions take place in standard FP buffers and may contain a range of different additives to prevent non-specific binding. A prototypical buffer may contain the following: phosphate buffered saline, NP40, bovine serum albumin, bovine gamma globulin, glycerol, or other agents to decrease background noise and increase specificity. Once mixed, the plate is placed in a Beckman DTX 880, and using the included FP (fluorescein) filter, set to a read time of around 1 second per well or other, depending on the fluorophore used. Polarization values are measured in millipolarizations units (mP) calculated using the equation: mP=[(Is−IsB)−(Ip−IpB]/[(Is−IsB)+(Ip−IpB)]×1000 [47-49]. Initial experiments generate dose response curves based upon the concentration of the antibody and OFA/iLRP. After that, excess unlabeled antibody can be used as a competitor to determine specificity and equilibrium. Additionally, the data generated from this can be used to back-calculate binding analysis plots (i.e., Scatchard or similar), and in turn, used as a method to determine the efficiency of antibodies. Once the initial conditions are determined, the FP method can be used to calculate the amount of OFA/iLRP present in different biofluids and tissue lysates.

Use In Flow Cytometric Analysis To Either Isolate/Separated OFA/iLRP Positive Cells Or To Determine The OFA/iLRP Positive Cancer Cell Load In The Blood To determine the total cancerous load of circulating hematologic type cancers, or to determine metastatic load, flow cytometry may be used. Briefly, a cell suspension or peripheral blood is obtained. The cell suspension is centrifuged 8 to 10 minutes at 300×g and the supernatant removed. The cells are washed in flow cytometry staining buffer (HBBS without phenol red, 0.1% sodium azide, and 1% bovine serum albumin) one time and resuspended at around 2×10^7 cells/ml or 50 to 100 μl of the cell suspension on the bottom of a 96-well round bottom plate or equivalent. To the cell suspension, fluoroscein isothiocyanate (FITC) or equivalent labeled OFA/iLRP antibody diluted in staining buffer is added. As a control for background, the cells are tested without any antibody, with an unlabeled isotype control antibody or equivalent (excess unlabeled antibody or competitor peptide). Cell suspension and appropriately diluted antibody is incubated for 20 to 60 min on ice or 4° C. with gentle mixing. The stained cell suspension is washed three times with 100 μl of staining buffer and centrifuged 3 to 10 min at 300 to 500×g. After the final wash, the cells are suspended in around 400 μl of staining buffer and stored in the dark, covered at 4° C. until analyzed. Additional steps may include counterstaining with propidium iodide to detect dead cells or the addition of a fixation step. Data is collected and analyzed following standard protocols [30, 39, 51], following the manufacturers instructions. It is expected that either the direct conjugation of FITC or detection using a biotin/strepavidin-FITC may be used to detect the number of OFA/iLRP positive cells in peripheral blood, cell suspension, or other source. The overall number of OFA/iLRP positive cells can provide insight into aggressiveness and/or progression of the OFA/iLRP positive diseases.

Alternative applications of this method can also be used to determine the metastatic load of breast cancer through the analysis of sentinel nodes. Briefly, sentinel nodes (or any lymph node close to the initial cancer lesion) are gently disrupted in 5 ml of staining buffer following standard protocols. The cell slurry is filtered through a 100 μm mesh, and washed about two times as above. The resultant cell suspension is used to quantify localized metastasis.

The Antibodies Can Displace OFA/iLRP Or Other Proteins Bound To OFA/iLRP

The location and design of the FREPRLLVVTDRADHQ-PLT (SEQ. ID. NO.: 7) antibodies allow for the possibility that the antibody can displace the interacting OFA/iLRP protein. Additionally, antibodies designed against other regions may be used to displace interacting proteins or prevent them from binding. The initial concentrates on the displacement of or the prevention of the homodimeric interaction of OFA/iLRP.

To test the possibility that the antibody can displace interacting OFA/iLRP molecules, two separate experiments are performed. First, OFA/iLRP dimer is purified following standard protocols that purify the dimer form of OFA/iLRP. The dimeric form of the protein is incubated with increasing concentrations of antibodies against the OFA/iLRP. After incubating 1 hour at 37° C. in standard antibody binding buffer (PBS containing NP-40, Tween-20, BSA, BGG, or other additives), the conversion of dimeric to monomeric forms by antibodies is determined by running on a non-denaturing polyacrylamide gel following standard protocols [37, 38].

A second method that can be used exploits putative changes in fluorescent polarization depending on molecular size. In the presence of the dimer, the primary FP is derived from antibody rotation alone. If the antibody replaces the dimer, there is a shift to monomer and the fluorescent polarization should change.

Fluorophores may additionally be used to quench or modify the emission spectra due to proximity. Two or more antibodies may be used to modify emission spectra or quench can be used to determine the state and/or stability of the OFA/iLRP molecule.

The Antibodies Are Used As A Cancer Treatment

The antibodies designed to target the OFA/iLRP sequences can be used as a form of treatment or possible prevention for OFA/iLRP positive diseases. For example, testing for the prevention or treatment of OFA/iLRP positive cancers could occur using similar animal model using standard cell lines. To test for the prevention of cancer OFA/iLRP, antibodies can be injected into a rodent (mouse or rat) prior to cancer challenge. To test for the treatment, OFA/iLRP antibodies can be injected after the cancer challenge. The cancer challenge is a range of different known cancerous cell lines, some adherent and some non-adherent. The cells are grown and introduced into a rodent model system. The amount of OFA/iLRP positive cancer cells can be quantified through a range of different methods. Additionally, adherent cells injected through the tail vein will have increased colonization of the lungs. The treatment and/or preventative abilities of the OFA/iLRP antibody can be calculated by the number of cancer cells present in the lungs of treated versus untreated animals. Additional controls may be the injection of non-specific isotype control antibodies at the same schedule as the OFA/iLRP antibodies. Additionally, the OFA/iLRP antibodies augment current cancer therapies. To decrease possible allergic reactions, the antibodies may be cloned and humanized following standard protocol prior to use in humans.

The Antibodies Can Alter Biological Function, Leading To Altered Effects Caused By OFA/iLRP Expressing Related Diseases The antibodies may alter the overall invasiveness or ability to bind to a standardized substrate. Standard cell lines can be tested following standard protocols. One test that is performed to determine the possible pharmacological affect on mammalian and non-mammalian cells is the effect on growth rate, for example, the growth of cells with and with out the peptides at a range of different concentrations, and to measure the affect on apoptosis, necrosis, and cell proliferation. OFA/iLRP positive cancer cells can be grown in vitro on a range of different basement membranes with the peptides at a range of doses. The effect of the peptides can be measured by a range of different methods including, but not limited to, DNA ladder, cell death detection ELISA, caspase measurement, TUNEL assay, Annexin-V membrane alterations, DNA stain, FAS, p53, cytotoxicity assay, cell proliferation, and cell viability following standard methods.

The peptides may have the ability to increase or decrease the invasiveness of a OFA/iLRP positive cancer cell. This can be measured by growing OFA/iLRP positive cells with and without a range of different concentrations of the peptide using a modified Boyden-chamber similar to several studies involving other proteins [52-55]. The peptides may also affect cell adhesion and can be measured using standard methods. Adherent cultured OFA/iLRP positive cancer cells are cultured in the presence of different extra-cellular matrix proteins (ECM) and with the peptides.

The cells are then assayed, following standard methods to determine the relative attachment of the cell lines in the presence of the peptides [56-59]. Several other commonly used techniques may be applied to determine the affect of OFA/iLRP on cell viability, proliferation, cell death, and apoptosis [37-39, 42].

The Antibodies Are Linked To Colloids To Have Anti-Cancer Activity Or To Provide An In Vivo Marker For Cancer The antibodies can be attached or cross-linked to a range of different colloids. For example, gold or silver colloid can be used to identify OFA/iLRP positive cells through resonant light scattering or alternative methods. Additional uses for the colloid would be one that oxygen-free radicals or similar can be induced. The colloidal agent linked to an antibody increases the probability and OFA/iLRP positive cancer cell is exposed to free radicals.

The Antibodies Are Linked To An X-Ray Opaque Dye, Or Similar Type Of Conjugate To Be Used With An X-Ray The antibody is conjugated to a radiopaque dye or similar [60]. The ability to detect a cancerous state early and accurately can help with patient treatment options. It may be possible to conjugate the antibody to a radiopaque dye or equivalent to increase the efficiency of current x-ray based techniques. Additionally, the antibody may be linked to a molecule that could be "tuned" to specific resonant frequencies to be detected by MRI. Possible conjugates include, but are not limited to, a chemically reactive gadolinium-based system that can be attached to antibodies similar to used for conjugation to fluorescent dyes. A commonly used technique is the addition of a tetrafluorophenyl (TFP) ester moiety that reacts with the primary amines found on antibodies. The unreacted TFP gadolinium can be removed using sized exclusion chromatography. In order to be used clinically in humans, the antibody may need to be humanized. The method described above would follow standard protocols.

As a proof of concept, there is no need for the animal model to have an active immune system, which allows for the use of standard techniques [61]. The initial work does not need to use x-rays but needs to demonstrate the ability of the OFA/iLRP antibodies to bind in vivo. The antibody or equivalent is conjugated to a fluorophore, colloid, enzyme conjugate, or other method that can be easily detected. The conjugated antibody is injected into the animal at a range of different doses, and at defined time-points, the induced tumors can be sampled to look for binding of the antibody. This binding can show that this can be used to target tumors for diagnostic imaging. Additional methods include the use of gold nanoparticles that can be coated with epoxy silane derivatives or similar for covalent linkages to the antibodies [62].

The Antibodies Are Linked To, And Conjugated With, Chemotherapeutic Agents And Directed To OFA/iLRP-Positive Cancer Cells In order to decrease the number of side effects associated with classical chemotherapy, a targeted approach may be taken. The use of the OFA/iLRP antibodies as a targeting agent for anti-cancer drugs may increase safety and efficacy of current therapies. A way to test the effectiveness of this and as a proof of concept, antibodies may be incorporated in a liposomal type system where the liposome contains a chemotherapeutic agent. To show targeting ability, OFA/iLRP cells, a mixture of OFA/iLRP cancer cells and normal human cells can be mixed in a cell culture plate. The mixture can be added and compared to the treatment of cells with similar dose of chemotherapeutic agent or liposome with isotype control antibodies incorporated. It is expected that the target approach would have a higher mortality of OFA/iLRP positive cells without as drastic an affect on normal cells. The effect can be determined through a range of different standard techniques. While standard chemotherapeutic agents can be used, another technique could use the attachment of radioactive molecules to the OFA/iLRP antibody. For example, the antibody is iodinated following standard protocols.

In addition to linking directly to the chemotherapeutic agent, creating a liposome with the antibodies agent, a polyacrylamide/agarose bead soaked in chemotherapeutic agent, the antibody can be attached to an alternative delivery method. It may be possible to have carbon nano-tubes or equivalent that can carry chemotherapeutic agents. When interacting with the OFA/iLRP positive cell, a signal could be provided to cause the nano-tubes to resonate and release the contained anti-cancer agent. The trigger can be a range of different methods. The antibodies can be linked to, and conjugated with, nano-carbon, nano-gold, and other nanotubes and nano-agents, and subjected to a micro-electro/radiowave-sensitive device or similar device in order to target OFA/iLRP-positive cancer cells. When directly linked between the antibody and the anti-cancer agent, a reactive linker molecule is targeted to release the anti-cancer agent. An example of this could be a linker between the antibody and the anti-cancer agent that is UV or x-ray cleavable. In the presence of x-rays (radiation therapy), the linker can cleave and release the anti-cancer drug. Another method uses a peptide linker with a protease cleavage site to be cleaved when in the tumor microenvironment.

The Antibodies Can Be Linked To, And Conjugated With, Other Proteins That Alters The Biological Function Of The Target Cells The antibody can only direct certain types of immune responses. The fusion of two distinct sequences to create DNA vaccinations have been used before [63]. This molecule is a hybrid of the OFA/iLRP antibody-binding region that is fused to a biologically active sequence that can modulate the tumor or surrounding area. A couple of possibilities are to clone the humanized OFA/iLRP antibody active region and fuse it to an immune system regulator, cell cycle regulator, or apoptosis-inducing protein sequence. To prevent non-specific events, the protein is engineered to remain inactive until in the tumor micro-environment. An OFA/iLRP antibody is fused to a protease cleavage site linker that is then attached to an apoptosis-inducing peptide or a small molecule to induce an immune response against the tumor. The fusion of two different molecules could allow for a multivalent antibody that can be targeted with increased specificity to cancer cells.

The Use of OFA/iLRP Antibodies With Microelectrofluidic Or Equivalent Devices Are Used Diagnostically Or As An Ongoing Screening Method The OFA/iLRP antibodies or active regions are coated onto microelectrofluidic devices to measure real-time OFA/iLRP expression in the blood stream. This device is self-contained to act as a monitoring device for cancer reassurance. The antibodies are coated on a film or other micro-device to allow for the detection of the cancer. It is possible to determine the amount bound based on a couple of methods. First, the antibody can be coated on a molecular cantilever that has a defined flow across it. As the real-time interaction between the antigen and antibody occur, there should be an increased torque on the coated lever. This, in turn, can be measured through changes in resistance or induction of electrical charge. A similar technique is used with a thin film coated with OFA/iLRP antibodies and when bound by the antigen, either the charge or interaction or change of tension on the film can be measured and correlated to changes in OFA/iLRP expression. These techniques are not limited to OFA/iLRP, but any cancer molecule can be used as a micro-implanted device that can be read by clinicians as needed to alert them to reoccurrence or metastatic disease progression.

The Use of OFA/iLRP Antibody Attached To Radioactivity, Fluorescent Or Equivalent Molecules To Aid The Medical Doctor In Excision of The Tumor As an aid to the surgeon during the excision of cancer, the use of OFA/iLRP antibodies are linked to a fluorophore, radioactive marker, dye or equivalent, allowing the surgeon to easily identify the cancerous growth. Additionally, this technique may be used to quickly identify lymph nodes that may contain metastatic disease, for example, an anti-cancer antibody linked to an appropriate conjugate to allow for identification, such as current radioactivity is used for sentinel node biopsy. After the injection, the patient is brought to surgery where the procedure occurs as usual. However, if it is difficult to find the cancer or to check for lymph nodes, a Geiger counter, UV, or other light source can be used which allows for rapid identification of the cancerous areas. The cancer is excised using the appropriate surgical treatment. This method can greatly aid in the identification/excision of cancer.

The Use Of The Antibodies For Immunoprecipitation

The OFA/iLRP antibodies are used for immunoprecipitation to identify novel therapeutic targets. Cell lysate is immunoprecipitated following standard protocols [37, 39]. The resultant proteins can be analyzed on SDS-PAGE, 2d gel electrophoresis, mass spectroscopy, or other methods. The resultant information may provide insight into possible OFA/iLRP-related mechanisms that can be used for clinical diagnostic or treatment.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Example 1

Method of Making OFA/iLRP Monoclonal Antibodies 2C6 and 3G7

OFA/iLRP monoclonal antibodies 2C6 and 3G7 were made at Precision Antibody using standard methods and protocols. The peptide of FREPRLLVVTDPRC (SEQ. ID. NO.: 8) was used to generate monoclonal antibody 3G7. The peptide of YRDPEEIEKEEQC (SEQ. ID. NO.: 9) was used to generate monoclonal antibody 2C6.

The synthesized peptides were conjugated to maleimide-activated KLH using standard protocols (Pierce/Thermo, Rockfork, Ill.). Once conjugated, the KLH-OFA peptides were used to immunize two different mice per peptide. After immunization, the serum was obtained via tail bleed and the serum was used to screen for antibody titer against BSA-conjugated peptides (FIG. 1). If positive against the peptide, an indirect ELISA using recombinant human OFA/iLRP was done to verify that that the antibodies would react with the protein. This was done to ensure that the antibody would react against small peptides as well as the full-length protein. After the reactivity against the peptide and protein was verified, the spleen cells were fused with a myeloma cell line and selected in 96-well culture plates. Viable colonies were kept alive and then screened against the peptide and OFA/iLRP (similar to above). The hybridoma tissue culture supernatants that had high activity against OFA/iLRP but not against BSA-coated wells were chosen for immunoglobulin classification (IgG or IgM). Any clones that were IgM were excluded from the screen and the IgG-producing hybridomas were grown following standard protocols. To further purify the antibodies from the medium, a protein G selection was done following standard protocols (Pierce/Thermo, Rockford, Ill.). The eluted antibodies concentration was determined using A260 absorbance and this was used for 2C6 and 3G7 antibody production.

Example 2

Analysis of Tail Bleeds for Activity Against rHu OFA

In this study, activity against recombinant full-length human OFA/iLRP was analyzed. Nunc-Immunostar MaxiSorp plates were coated with OFA/iLRP protein at a concentration of 10 µg/ml in PBS with sodium azide. Plates were incubated at 37° C. for 2 hours. Plates were washed with water 3 times, then blocked for at least an hour with 5% non-fat dry milk (NFDM) in PBS-t. Plates were washed 3 times with PBS-t tail bleeds and positive controls were added in 5% NFDM. Plates were incubated overnight at 4° C. with shaking. Plates were washed as above and incubated for 1 hour at room temperature in universal secondary antibody diluted 1:100 in 5% NFDM. Plates were washed and incubated for 30 minutes at room temperature with Streptavidin-HRP (1:200 R&D systems). Plates were washed and 200 µl SIGMA FAST™ OPD was added to each well. Plates were observed for reaction and the plate was stopped with 50 µl of stop (2n $H_2SO_4$) while there was still low background. Plates were read and analyzed on a SpectraMax 384 following the standard protocol on the instrument for basic endpoint ELISA w/OPD and acid stop.

Figure 2:
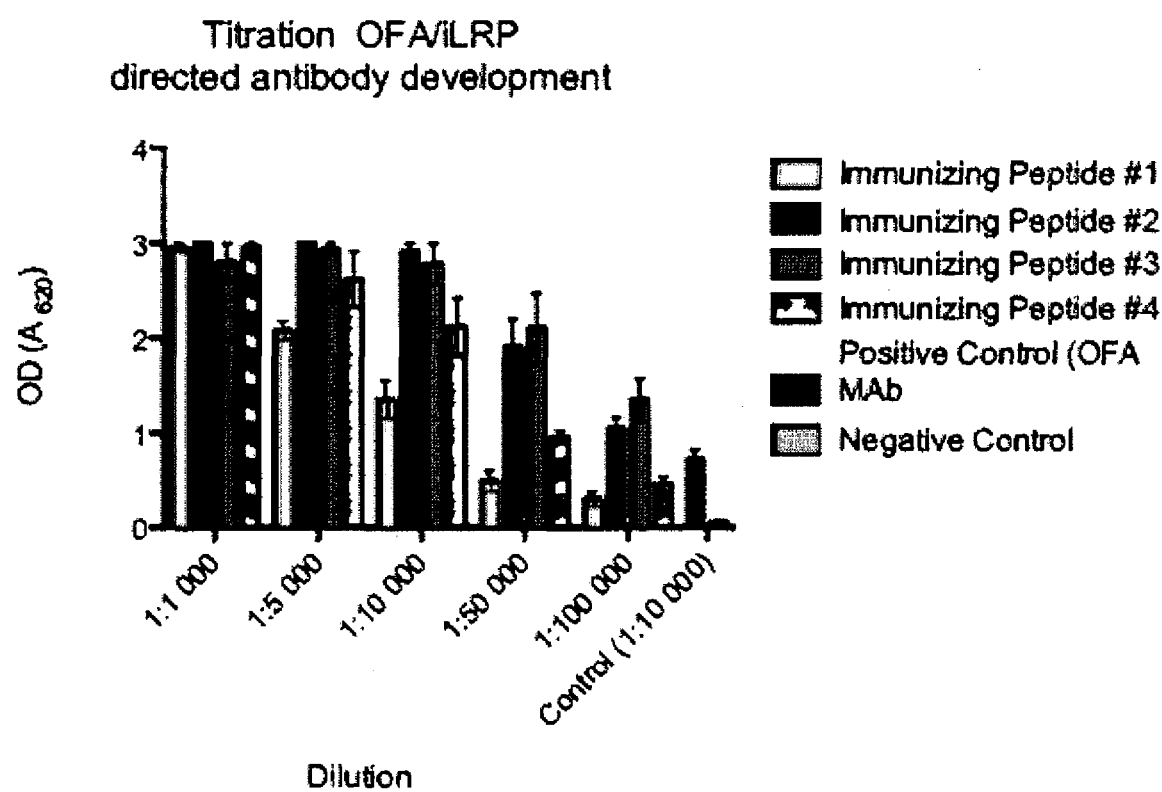
FIG. 2. Titration of OFA/iLRP polyclonal serum against OFA/iLRP. Detection of OFA/iLRP antibody antigen interaction using a biotinylated secondary antibody. Prism Graph of the Absorbance read at A620 on a Beckman DTX 880.

All of the immunizing peptides designed against OFA/iLRP (Table 2) produced tail bleed serum that can react with the recombinant full-length OFA protein. When compared to previously developed monoclonal antibodies provided by Drs. Coggin, Rohrer and Barsoum (Positive control), the tail bleed serum performed similar or slightly better (FIG. 2) despite the monoclonal antibody being at a concentration greater than 2 mg/ml. This experiment further demonstrates the use of OFA/iLRP as a capture antigen to determine antibody titre of patient and diagnostic samples.

The results show that peptide-derived antibodies against OFA/iLRP can recognize the recombinant full-length protein. Additionally, coating of the recombinant full-length OFA onto a plate can be used as a screening method for further antibody development or monitoring of anti-OFA immune responses.

Example 3

Indirect ELISA of rOFA/iLRP to Determine the Reactivity of Monoclonal Antibodies In this study, the immunoreactivity of monoclonal antibodies designed against specific regions of OFA/iLRP to the recombinant OFA/iLRP was determined. Briefly, Immulon 4HBX plates were coated with OFA/iLRP protein at a concentration of 2 µg/ml in PBS. Plates were incubated at 4° C.

overnight. Plates were washed with water three times, then blocked for at least an hour with 1% BSA in PBS-t. Plates were washed three times with PBS-t and a 5-fold dilution series of the monoclonal antibodies was run along 8 wells with a high concentration of 1:10 and a low of 1:781,250. Plates were incubated overnight at 4° C. with shaking. Plates were washed as above and incubated for 1 hour with biotinylated anti-mouse IgG secondary at 1:50,000. Plates were washed and incubated for 30 minutes at room temperature with Streptavidin-HRP (1:250,000). Plates were washed and 100 μl TMB Two Component HRP microwell substrate (BioFX Laboratories, Owings Mills, Md.) was added to each well. Plates were observed for reaction and the plate was stopped with 50 μl of stop (2n H2SO4) while there was still low background. Plates were read and analyzed on a SpectraMax following the standard protocol on the instrument for basic endpoint ELISA w/ HRP and TMB.

Figure 3:
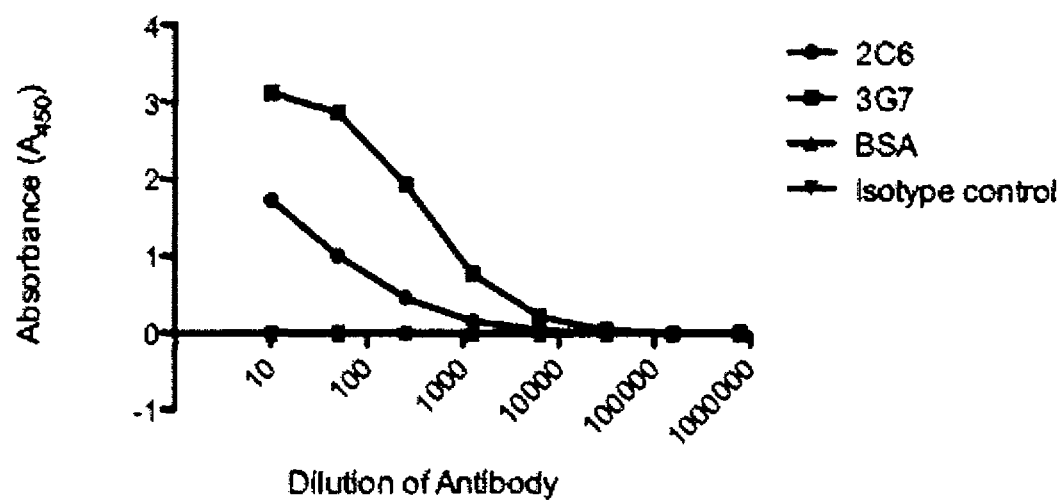
FIG. 3. Dilution curve of monoclonal antibodies 2C6 and 3G7 run on an indirect ELISA against OFA/iLRP.

The results in FIG. 3 show a dilution curve of the monoclonal antibodies 2C6 and 3G7 run on an indirect ELISA against rHu OFA/iLRP (n=4). An 8-point dilution series with 5-fold dilutions starting at 1:10 and ranging down to 1:781,250 show that there is a strong reaction of the monoclonal 2C6 to the OFA and there is a dynamic range of detection using the 2C6 antibody in this assay.

FIG. 3 also shows a dilution curve of the monoclonal antibody 3G7 run on an indirect ELISA against OFA/iLRP. An 8-point dilution series identical to that above shows that there is strong reaction of the monoclonal 3G7 to the OFA and there is a dynamic range of detection using the 3G7 antibody in this assay (n=4).

This data indicates that both of these monoclonal antibodies (2C6 and 3G7) have the ability to recognize and bind to the full-length OFA/iLRP. This data demonstrates that the engineered antibodies can be used to detect OFA in a specific manner that can be used for a wide range of downstream diagnostic tests. They also can be used as standards to look for the presence of anti-OFA antibodies in a range of biofluids.

Example 4

Sandwich ELISA of rOFA/iLRP to Determine the Reactivity of Monoclonal Antibodies Immulon 4HBX plates were coated with 2C6 monoclonal antibody at a concentration of 10 μg/ml in PBS. Plates were incubated at room temperature overnight. Plates were washed with water three times, then blocked for an hour with 1% BSA in PBS-t. Plates were washed three times with PBS-t and a 2-fold dilution series of OFA/iLRP was run along 8 wells with a high concentration of 5000 ng/ml and a low concentration of 78.125 ng/ml. OFA/iLRP standards were prepared in 5% BSA in PBS to simulate serum concentrations. Plates were incubated 2 hours at room temperature with shaking. Plates were washed as above and incubated for 2 hours with biotinylated 3G7 monoclonal antibody. Plates were washed and incubated for 30 minutes at room temperature with Streptavidin-HRP (1:200) (R&D). Plates were washed and 100 μl of TMB Two Component HRP microwell substrate (BioFX Laboratories, Owings Mills, Md.) was added to each well. Plates were observed for reaction and the plate was stopped with 50 μl of stop (2n $H_2SO_4$) while there was still low background. Plates were read and analyzed on a SpectraMax at 450 nm following the standard protocol on the instrument for basic endpoint ELISA w/ HRP and TMB.

Figure 4:
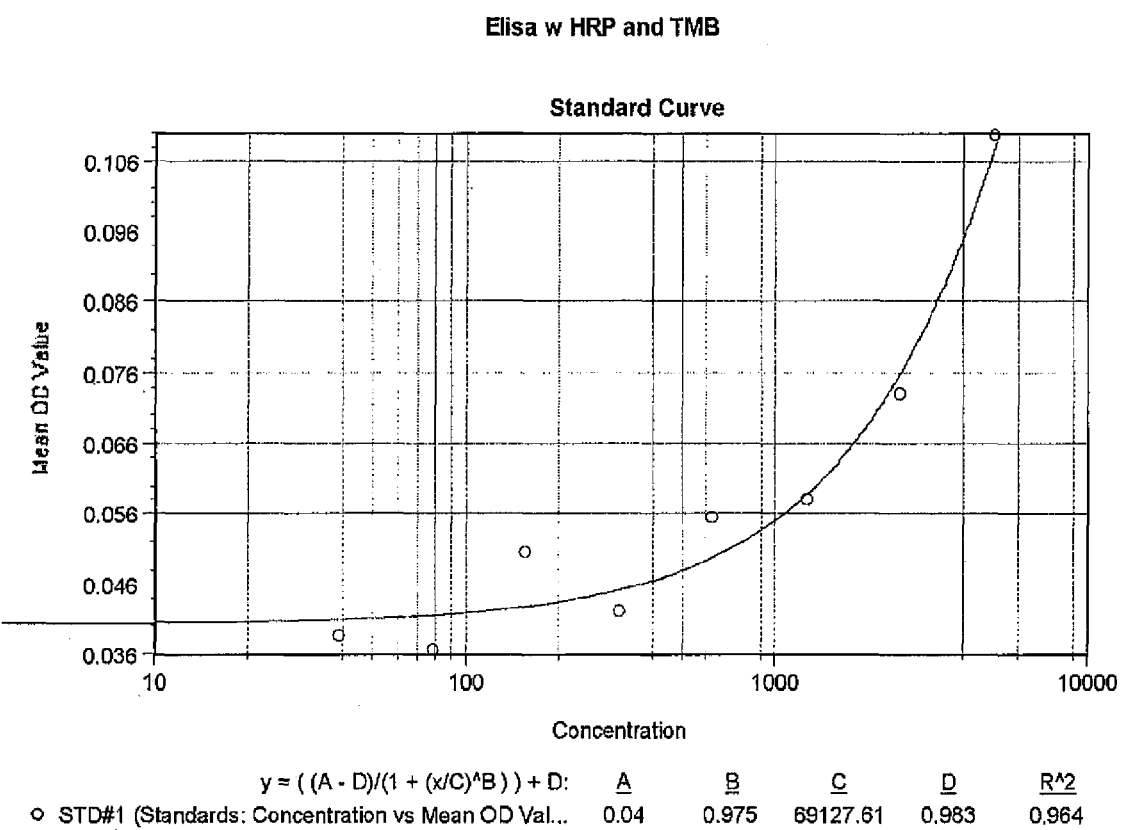
FIG. 4. Sandwich ELISA of rOFA/iLRP to determine the reactivity of monoclonal antibodies (2C6 and 3G7). Raw data was plotted on a semi-log graph and cure fitting was done using the 4-parameter logistic following standard protocols (SoftMax Pro 4.3.1 LS).

FIG. 4 shows a standard curve of a wide range of concentration of OFA/iLRP and the ability of our monoclonal antibodies to detect it using a sandwich ELISA. This data shows that both of these monoclonal antibodies (2C6 and 3G7) have the ability to recognize and bind to the full-length OFA/iLRP in a manner that can be detected using sandwich ELISAs. When reversed (i.e., 3G7 capture/2C6 detection), a similar result was seen but the reaction absorbance was significantly lower than when using the 2C6 as a capture antibody (date not shown). Likewise, this data demonstrates that the engineered antibodies can be used to detect OFA in a specific manner that can be used for a wide range of downstream diagnostic tests. This type of ELISA can be used to look for the presence of OFA/iLRP in a range of biofluids and tissue lysates. Additionally, this technology may be applied for inclusion/exclusion criteria for OFA/iLRP-based therapies or used as a cancer diagnostic. The antibodies were designed against conserved regions of the protein and should cross-react with all species that express OFA/iLRP.

Example 5

Fluorescent Polarization of Oncofetal Antigen Immature Laminin Receptor Using Peptide Derived Monoclonal Antibodies This experiment demonstrates the usability of the 2C6 clone of the OFA/iLRP in fluorescent polarization. To simulate a serum sample, all standards were diluted in 5% Bovine Serum Albumin (BSA) in phosphate buffered saline. The experiments were based in part on the HSP 90 work, but a fluorsceine-5-maleimide-labeled antibody was used instead of geldanamycin-BODIPY, a small fluorescent molecule that can bind HSP 90 [49, 45].

OFA/iLRP monoclonal antibodies 2C6 and 3G7 were labeled with Fluorescein-5-Maleimide (Pierce/Thermo, Rockford, Ill.) following standard protocols. The unbound dye was removed using standard dye removal columns following the manufacturer's protocols. After labeling the antibody, it was used in fluorescent polarization experiments.

Figure 5:
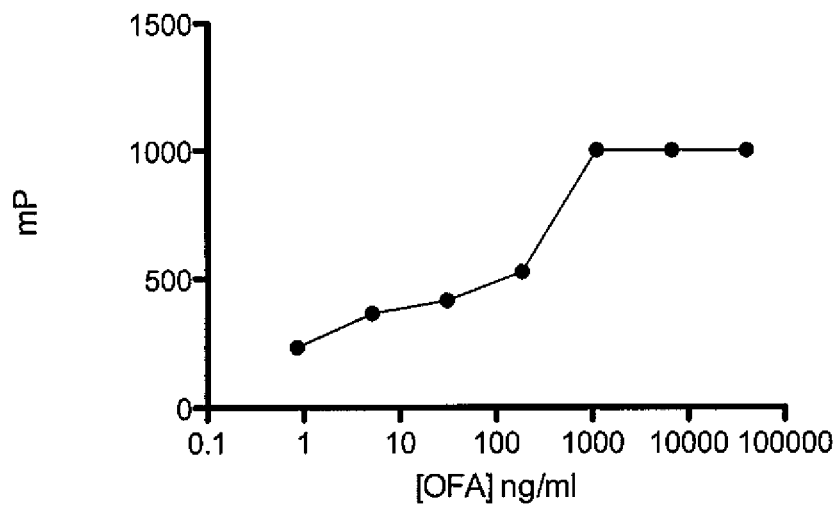
FIG. 5. Fluorescent polarization of OFA/iLRP. (A) Raw data was plotted on a log x-axis. (B) Curve fit data using four-parameter logistic ($r^2$=0.975) n=2.
Figure 5:
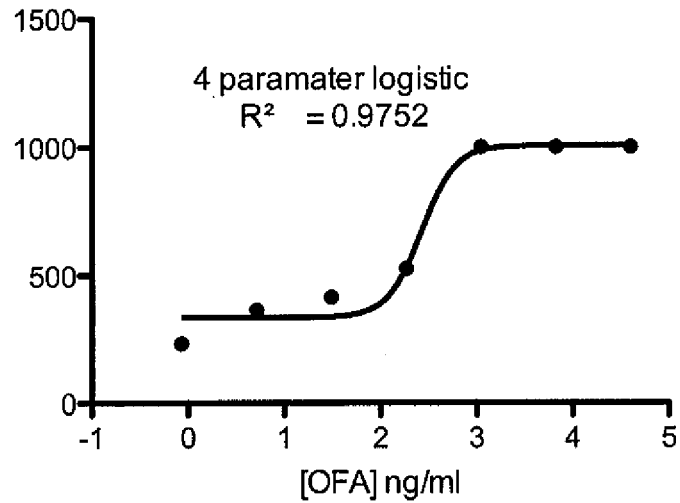

OFA/iLRP was diluted to 40000 ng/ml in 5% BSA in PBS and 50 μl was added to the top well and diluted 6-fold in 5% BSA in PBS in a 96-well black plate (Cliniplate, Thermo Scientific). A high concentration of serum albumin (>5% serum albumin) was used to simulate serum concentrations. The labeled antibody was diluted to 20 μg/ml in PBS with 0.1% normal human plasma and 0.01% Tween-20. The diluted antibody solution (500) was dispensed into the wells, mixed, sealed, covered from light and incubated overnight at 4° C. The plates were allowed to adjust to room temp and the fluorescent polarization was measured on a DTX-880 (Beckman Instruments, Palo Alto, Calif.). The manufacturer fluorescent protocol was used except fluorescent integration time of 0.0001 s. The data was exported to excel and mP was calculated as outlined previously [49]. The raw data was plotted on a log x-axis (FIG. 5A) using Prism 5.0 (GraphPad Software, Inc), analyzed using one-way ANOVA to compare the background to the calculated mP values, and transformed to allow for a four-parameter logistic (FIG. 5B) ($r^2$=0.975) n=2. The concentrations of OFA in 5% BSA/PBS ranged 40000 to 0.85 ng/ml and showed a range from less than 1000 ng/ml (due to saturation) to less than 30.86 ng/ml (FIG. 5A). At concentrations above 1000 ng/ml, the signal became saturated, and below 30.6 ng/ml (5.1 ng/ml), the signal was not significantly different than the background when the data is transformed and a four-parameter logistic is performed and r2>0.95 (FIG. 5B).

The results demonstrate that the peptide-derived OFA/iLRP antibodies can be used to determine OFA/iLRP concentration using fluorescent polarization. This data provided by the standard curve had an acceptable $r^2$ value that can be used to calculate unknowns from serum, plasma, tissue lysate, or any soluble source contain OFA/iLRP.

Example 6

Immunohistochemical Staining of OFA/iLRP

The purpose of this study was to analyze the ability of our monoclonal antibodies to detect OFA/iLRP in formalin-fixed paraffin-embedded (FFPE), 6 micron thick tumor sections with limited reaction in normal adjacent tissue.

Experiments were performed following the protocol provided with the MaxTag Histo kit for use with mouse Primary Antibody (Rockland Immunochemicals, Gilbertsville, Pa.). Briefly, FFPE 6 micron tumor slides were de-paraffinized with xylenes and then rehydrated with decreasing concentrations of ethanol (EtOH), then diluted with water, and finally placed in PBS. All incubation steps were carried out in a humidified chamber. The area on the slide containing the tissue was marked with a PAP pen, and then blocked for 5 minutes in 1% hydrogen peroxide and 1% normal goat serum in PBS to remove endogenous peroxidase activity. The slides were then washed three times in PBS for 5 minutes. The primary antibody was diluted 1:250 in PBS+1% normal goat serum and incubated on the slide at 4° C. overnight. The previous experiments were run at primary antibody dilutions of 1:10 and 1:50, and had too high of a background stain. (Data not shown). The slides were then washed three times for five minutes in PBS, then the secondary antibody provided in the kit was added, and they were incubated for 30 minutes at room temperature. The slides were washed again and the diluted streptavidin peroxidase reagent from the kit was added and incubated for 30 minutes at room temperature. The slides were washed again and the supplied DAB reagent was added and incubated for 15 minutes while monitoring for color development. The DAB reaction was allowed to incubate 10 minutes longer than the manufacturer's recommendations to determine the true background staining of the normal adjacent tissue. The slides were then washed three times for two minutes with distilled water. Hematoxylin counterstain was added and the slides were incubated for five minutes. The slides were washed again three times for two minutes with water, dehydrated with 100% EtOH four times for two minutes each, and then cleared with four changes of xylene for two minutes each. The tissues were observed under a microscope and evaluated with a positive reaction being visualized as a brown precipitate and nuclei staining light blue.

Figure 6:
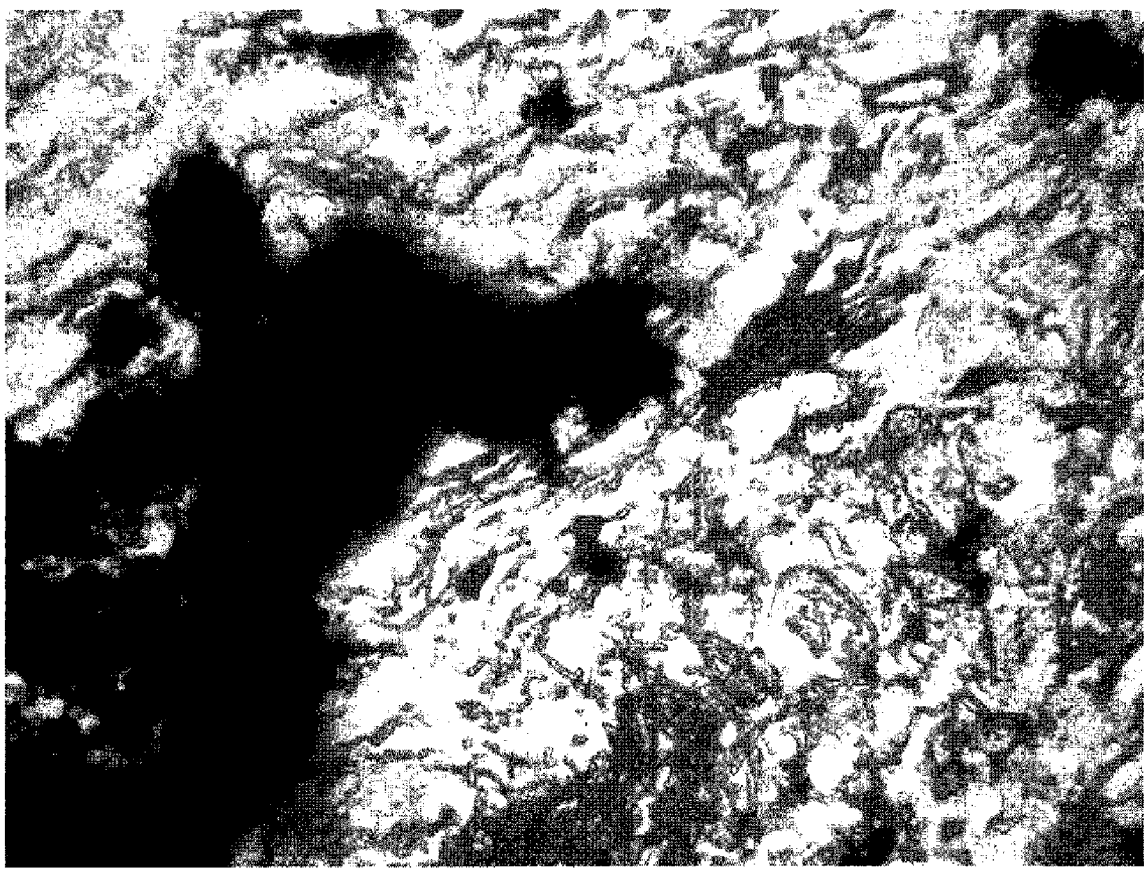
FIG. 6. IHC staining of human invasive ductal carcinoma, moderately differentiated, T2N1M0 using 3G7 monoclonal antibody for the primary antibody reaction. The very dark regions are where cells are expressing large amounts of OFA/iLRP and a thick precipitate was deposited.

The stains were run on multiple tumor types. The slide shown in FIG. 6 is a representative section that shows breast invasive ductal carcinoma, moderately differentiated, T2N1M0, that has been stained with the 3G7 monoclonal antibody as the primary antibody. Staining of the slide ranges from very dark, black precipitate to very light, similar to isotype control run slides (not shown). OFA/iLRP expression has been seen in all tumor types tested to date.

The results show that the monoclonal antibodies are amenable to IHC staining protocols and may be used in a range of different experimental and diagnostic applications. One potential application is for applicability for OFA/iLRP therapy or as a screening/diagnostic test. Since OFA/iLRP is specifically designed against conserved regions, these antibodies should cross-react with all species.

Example 7

The Effect of OFA/iLRP Monoclonal Antibodies on Cell Viability

The goal of this experiment is to determine if the monoclonal antibodies designed against the OFA/iLRP have any affect on cell viability. Due to the nature of OFA/iLRP, it was expected that monoclonal antibodies that are designed to disrupt the OFA|OFA to LR conversion or that inhibit other protein|protein interactions that will have activity.

All cells were grown in RPMI 1640 with L-glutamine; 100 I.U. Penicillin; 100 μg/ml Streptomycin and 10% fetal calf serum at 37° C. in a humid chamber (Mediatech, Inc. Manassas, Va.). DU 145 cells were obtained from American Type Culture Collection (ATCC, Manassas, Va.) and grown in media following standard protocols. DU145 cells were grown to between 75 and 85% density and collected following standard protocols and counted using a modified Neubauer brightline hemacytometer and suspended at 400,000 cell/ml.

Monoclonal antibodies (2C6 and 3G7) were dissolved in complete medium. After being diluted to appropriate concentration, 50 μl was dispensed into a 96-well assay plate, either coated with laminin/entactin complex (50 μg/ml) or untreated (Black with clear bottom) (Corning Life Sciences, Corning, N.Y.), and 50 μl of cells (20,000 cells/well) grown overnight. 20 μl of CellTiter-Blue ((Promega, Madison, Wis.)) was added to the cells and they were incubated for an additional two hours at 37° C. The cells were read on a DTX-880 (Beckman Inc.) following standard fluorescent protocols with an integration time of 0.001 sec. To determine if caspase activity was induced, Caspase 3/7 activity was determined using ApoOne assay (Promega, Madison, Wis.). The data was exported to Excel and then to Prism 5.0 (GraphPad Software, Inc), where it was plotted, and analyzed for statistical differences between the background controls (diluents used for the peptide) using a one-way ANOVA. To determine the difference between the control group (0) and the treatments, a Dunnets post test was performed. Any $p<0.05$ (*) was considered to be significant.

Figure 7:
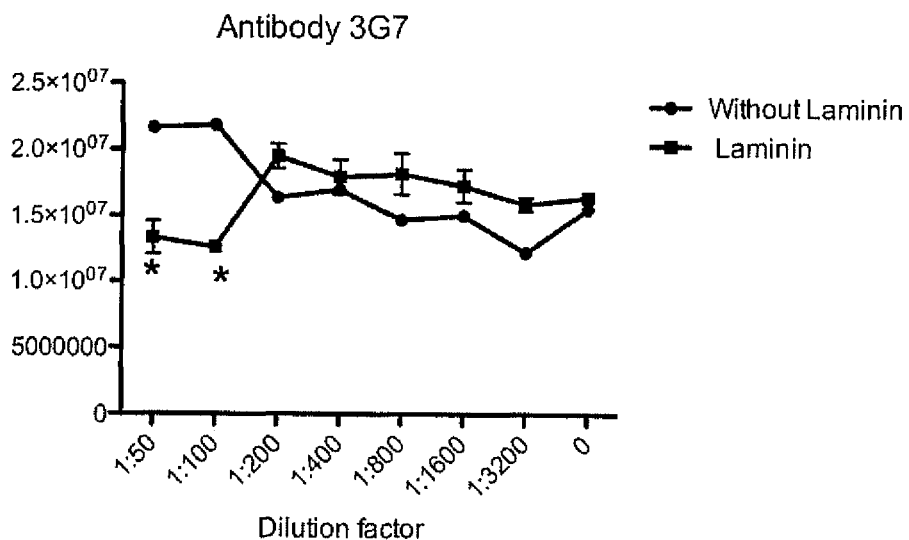
FIG. 7. The effect of 2C6 and 3G7 antibodies on cell viability was measured using CellTiter Blue. The decreased viability caused by the addition of antibodies is indicated by a lower fluorescent signal. The effect of the antibodies and requirement for laminin was determined by growing on either laminin/entactin coated or untreated plates.
Figure 7:
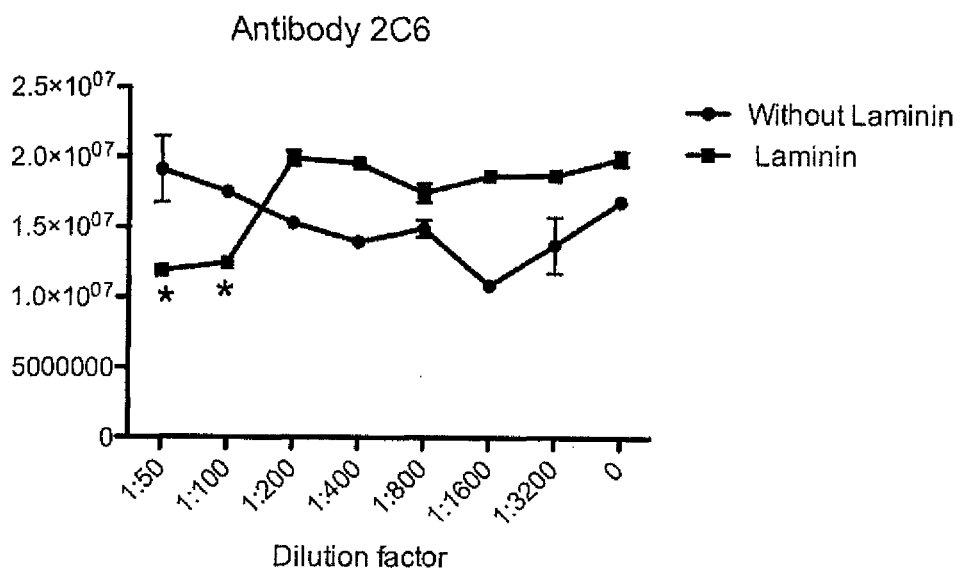

All of the DU145 cells grew on either the uncoated or Laminin/Entactin-coated 96-well plates. In the presence of either 2C6 or 3G7, there was an affect on cell viability (FIG. 7 A and B). When statistically analyzed by a one-way ANOVA, the 2C6 and 3G7 antibodies while at higher concentrations, caused a decreased viability when compared to the control group. However, considering the concentration differences between 3G7 (0.32 mg/ml) and 2C6 (1.29 mg/ml), 3G7 appears to have greater activity. No significant difference was seen in any group in the ApoOne Caspase 3/7 assay.

When DU145 cells were grown in the presence of either antibody, it appears to have had a significant affect on cell viability when compared to PBS alone. There was no Caspase 3/7 activation and no significant change in ApoOne assay was seen. This indicates that OFA/iLRP antibodies may have the ability to be used as an anticancer therapy. Many modifications and variations of the invention as herein before set forth can be made without departing from the spirit and scope thereof, and therefore only such limitations should be imposed as are indicated by the appended claims.

All patent and literature references cited in the present specification are hereby incorporated by reference in their entirety.

REFERENCES

1. Lesot, H., U. Kuhl, and K. V. Mark, Isolation of a laminin-binding protein from muscle cell membranes. EMBO J, 1983. 2(6): p. 861-865.

2. Malinoff, H. L. and M. S. Wicha, Isolation of a cell surface receptor protein for laminin from murine fibrosarcoma cells. J Cell Biol, 1983. 96(5): p. 1475-9.
3. Rao, N. C., et al., Isolation of a tumor cell laminin receptor. Biochem Biophys Res Commun, 1983. 111(3): p. 804-8.
4. Biragyn, A., et al., Tumor-associated embryonic antigen-expressing vaccines that target CCR6 elicit potent CD8+ T cell-mediated protective and therapeutic antitumor immunity. J Immunol, 2007. 179(2): p. 1381-8.
5. Castronovo, V., et al., Immunodetection of the metastasis-associated laminin receptor in human breast cancer cells obtained by fine-needle aspiration biopsy. Am J Pathol, 1990. 137(6): p. 1373-81.
6. Coggin, J. H., Jr., A. L. Barsoum, and J. W. Rohrer, 37 kiloDalton oncofetal antigen protein and immature laminin receptor protein are identical, universal T-cell inducing immunogens on primary rodent and human cancers. Anticancer Res, 1999. 19(6C): p. 5535-42.
7. Coggin, J. H., Jr., J. W. Rohrer, and A. L. Barsoum, A new immunobiological view of radiation-promoted lymphomagenesis. Int J Radiat Biol, 1997. 71(1): p. 81-94.
8. Coggin, J. H., Jr., J. W. Rohrer, and A. L. Barsoum, True immunogenicity of oncofetal antigen/immature laminin receptor protein. Cancer Res, 2004. 64(13): p. 4685; author reply 4685.
9. Coggin, J. H., Jr., et al., 44-kd oncofetal transplantation antigen in rodent and human fetal cells. Implications of recrudescence in human and rodent cancers. Arch Otolaryngol Head Neck Surg, 1993. 119(11): p. 1257-66.
10. Friedrichs, B., et al., Humoral immune responses against the immature laminin receptor protein show prognostic significance in patients with chronic lymphocytic leukemia. J Immunol, 2008. 180(9): p. 6374-84.
11. Giannopoulos, K. and M. Schmitt, Targets and strategies for T-cell based vaccines in patients with B-cell chronic lymphocytic leukemia. Leuk Lymphoma, 2006. 47(10): p. 2028-36.
12. Gussack, G. S., et al., Human squamous cell carcinoma lines express oncofetal 44-kD polypeptide defined by monoclonal antibody to mouse fetus. Cancer, 1988. 62(2): p. 283-90.
13. Holtl, L., et al., Immunotherapy of metastatic renal cell carcinoma with tumor lysate-pulsed autologous dendritic cells. Clin Cancer Res, 2002. 8(11): p. 3369-76.
14. Jackers, P., et al., Isolation from a multigene family of the active human gene of the metastasis-associated multifunctional protein 37LRP/p40 at chromosome 3p21.3. Oncogene, 1996. 13(3): p. 495-503.
15. Karpatova, M., et al., Shedding of the 67-kD laminin receptor by human cancer cells. J Cell Biochem, 1996. 60(2): p. 226-34.
16. Magnifico, A., et al., Peptide G, containing the binding site of the 67-kDa laminin receptor, increases and stabilizes laminin binding to cancer cells. J Biol Chem, 1996. 271(49): p. 31179-84.
17. Menard, S., E. Tagliabue, and M. I. Colnaghi, The 67 kDa laminin receptor as a prognostic factor in human cancer. Breast Cancer Res Treat, 1998. 52(1-3): p. 137-45.
18. Rohrer, J. W., et al., Human breast carcinoma patients develop clonable oncofetal antigen-specific effector and regulatory T lymphocytes. J Immunol, 1999. 162(11): p. 6880-92.
19. Rohrer, S. D., et al., Expression of 44-kilodalton oncofetal antigen as a premalignancy marker in X irradiation-induced murine T-cell lymphoma. J Natl Cancer Inst, 1992. 84(8): p. 602-9.
20. Sanjuan, X., et al., Overexpression of the 67-kD laminin receptor correlates with tumour progression in human colorectal carcinoma. J Pathol, 1996. 179(4): p. 376-80.
21. Siegel, S., et al., In-vivo detectable antibodies directed against the oncofetal antigen/immature laminin receptor can recognize and control myeloma cells—clinical implications. Leukemia, 2008. 22(11): p. 2115-8.
22. Siegel, S., et al., Identification of HLA-A*0201-presented T cell epitopes derived from the oncofetal antigen-immature laminin receptor protein in patients with hematological malignancies. J Immunol, 2006. 176(11): p. 6935-44.
23. Siegel, S., et al., Induction of cytotoxic T-cell responses against the oncofetal antigen-immature laminin receptor for the treatment of hematologic malignancies. Blood, 2003. 102(13): p. 4416-23.
24. Taraboletti, G., et al., Enhancement of metastatic potential of murine and human melanoma cells by laminin receptor peptide G: attachment of cancer cells to subendothelial matrix as a pathway for hematogenous metastasis. J Natl Cancer Inst, 1993. 85(3): p. 235-40.
25. Viacava, P., et al., The spectrum of 67-kD laminin receptor expression in breast carcinoma progression. J Pathol, 1997. 182(1): p. 36-44.
26. Wewer, U. M., et al., Altered levels of laminin receptor mRNA in various human carcinoma cells that have different abilities to bind laminin. Proc Natl Acad Sci USA, 1986. 83(19): p. 7137-41.
27. Zelle-Rieser, C., et al., Expression and immunogenicity of oncofetal antigen-immature laminin receptor in human renal cell carcinoma. J Urol, 2001. 165(5): p. 1705-9.
28. Jamieson, K. V., et al., Crystal structure of the human laminin receptor precursor. J Biol Chem, 2008. 283(6): p. 3002-5.
29. Liotta, L. A., et al., Monoclonal antibodies to the human laminin receptor recognize structurally distinct sites. Exp Cell Res, 1985. 156(1): p. 117-26.
30. Payne, W. J., Jr. and J. H. Coggin, Jr., Mouse monoclonal antibody to embryonic antigen: development, cross-reactivity with rodent and human tumors, and preliminary polypeptide characterization. J Natl Cancer Inst, 1985. 75(3): p. 527-44.
31. Coggin, J. H., Jr., et al., Radiation-induced lymphoblastic lymphomas/leukemias and sarcomas of mice express conserved, immunogenic 44-kilodalton oncofetal antigen. Am J Pathol, 1988. 130(1): p. 136-46.
32. Barsoum, A. L. and J. H. Coggin, Jr., Immunogenicity of a soluble partially purified oncofetal antigen from murine fibrosarcoma in syngeneic mice. J Biol Response Mod, 1989. 8(6): p. 579-92.
33. Castronovo, V., G. Taraboletti, and M. E. Sobel, Functional domains of the 67-kDa laminin receptor precursor. J Biol Chem, 1991. 266(30): p. 20440-6.
34. Barsoum, A. L. and J. H. Coggin, Jr., Isolation and partial characterization of a soluble oncofetal antigen from murine and human amniotic fluids. Int J Cancer, 1991. 48(2): p. 248-52.
35. Davis, C. M., et al., Identification and partial characterization of laminin binding proteins in immature rat Sertoli cells. Exp Cell Res, 1991. 193(2): p. 262-73.
36. Ardini, E., et al., Co-regulation and physical association of the 67-kDa monomeric laminin receptor and the alpha6beta4 integrin. J Biol Chem, 1997. 272(4): p. 2342-5.
37. Ausubel, F. M., Short protocols in molecular biology: a compendium of methods from Current protocols in molecular biology. 5th ed. 2002, [Hoboken, N.J.]: J. Wiley.

38. Coligan, J. E., Short protocols in protein science: a compendium of methods from Current protocols in protein science. 2003, [Hoboken, N.J.]: Wiley. 1 v. (various pagings).
39. Coligan, J. E., Short protocols in immunology: a compendium of methods from current protocols in immunology. 2005, Hoboken, N.J.: John Wiley & Sons. 1 v. (various pagings).
40. Ford, C. L., L. Randal-Whitis, and S. R. Ellis, Yeast proteins related to the p40/laminin receptor precursor are required for 20S ribosomal RNA processing and the maturation of 40S ribosomal subunits. Cancer Res, 1999. 59(3): p. 704-10.
41. Coggin, J. H., Jr., et al., Contemporary definitions of tumor specific antigens, immunogens and markers as related to the adaptive responses of the cancer-bearing host. Anticancer Res, 2005. 25(3c): p. 2345-55.
42. Bonifacino, J. S., Short protocols in cell biology: a compendium of methods from Current protocols in cell biology. 2004, Hoboken, N.J.: John Wiley. 1 v. (various pagings).
43. Banks, P., M. Gosselin, and L. Prystay, Impact of a red-shifted dye label for high throughput fluorescence polarization assays of G protein-coupled receptors. J Biomol Screen, 2000. 5(5): p. 329-34.
44. Banks, P., M. Gosselin, and L. Prystay, Fluorescence polarization assays for high throughput screening of G protein-coupled receptors. J Biomol Screen, 2000. 5(3): p. 159-68.
45. LeTilly, V. and C. A. Royer, Fluorescence anisotropy assays implicate protein-protein interactions in regulating trp repressor DNA binding. Biochemistry, 1993. 32(30): p. 7753-8.
46. Parker, G. J., et al., Development of high throughput screening assays using fluorescence polarization: nuclear receptor-ligand-binding and kinase/phosphatase assays. J Biomol Screen, 2000. 5(2): p. 77-88.
47. Tjandra-Maga, B., et al., Comparison of cyclosporin A measurement in whole blood by six different methods. J Clin Chem Clin Biochem, 1990. 28(1): p. 53-7.
48. Bittman, R. and S. A. Fischkoff, Fluorescence studies of the binding of the polyene antibiotics filipin 3, amphotericin B, nystatin, and lagosin to cholesterol. Proc Natl Acad Sci USA, 1972. 69(12): p. 3795-9.
49. Kim, J., et al., Development of a fluorescence polarization assay for the molecular chaperone Hsp90. J Biomol Screen, 2004. 9(5): p. 375-81.
50. Olle, E. W., et al., Development of an internally controlled antibody microarray. Mol Cell Proteomics, 2005. 4(11): p. 1664-72.
51. Coggin, J. H., Jr., Classification of tumor-associated antigens in rodents and humans. Immunol Today, 1994. 15(5): p. 246-7.
52. Aznavoorian, S., et al., Molecular aspects of tumor cell invasion and metastasis.
Cancer, 1993. 71(4): p. 1368-83.
53. Carroll, D. K., et al., p63 regulates an adhesion programme and cell survival in epithelial cells. Nat Cell Biol, 2006. 8(6): p. 551-61.
54. Ekblom, P., P. Lonai, and J. F. Talts, Expression and biological role of laminin-1. Matrix Biol, 2003. 22(1): p. 35-47.
55. Hood, J. D. and D. A. Cheresh, Role of integrins in cell invasion and migration. Nat Rev Cancer, 2002. 2(2): p. 91-100.
56. Horwitz, A. F. and T. Hunter, Cell adhesion: integrating circuitry. Trends Cell Biol, 1996. 6(12): p. 460-1.
57. Hynes, R. O., The dynamic dialogue between cells and matrices: implications of fibronectin's elasticity. Proc Natl Acad Sci USA, 1999. 96(6): p. 2588-90.
58. Li, S., et al., Matrix assembly, regulation, and survival functions of laminin and its receptors in embryonic stem cell differentiation. J Cell Biol, 2002. 157(7): p. 1279-90.
59. Stupack, D. G., Integrins as a distinct subtype of dependence receptors. Cell Death Differ, 2005. 12(8): p. 1021-30.
60. Debbage, P. and W. Jaschke, Molecular imaging with nanoparticles: giant roles for dwarf actors. Histochem Cell Biol, 2008. 130(5): p. 845-75.
61. Biragyn, A. and L. W. Kwak, Models for lymphoma. Curr Protoc Immunol, 2002. Chapter 20: p. Unit 20 6.
62. Hainfeld, J. F., et al., Gold nanoparticles: a new X-ray contrast agent. Br J Radiol, 2006. 79(939): p. 248-53.
63. Biragyn, A., et al., Genetic fusion of chemokines to a self tumor antigen induces protective, T-cell dependent antitumor immunity. Nat Biotechnol, 1999. 17(3): p. 253-8.

TABLE 1

List of different putative epitopes for antibody generation
Possible Antigenic Regions for Development of OFA/iLRP antibodies Initial Peptides of Interest ALDVLQM                 DVLKFLAAGT
(SEQ. ID. NO.: 10)      (SEQ. ID. NO.: 11)
EQYIYK                  FREPRLLVVTDPRADHQPLT
(SEQ. ID. NO.: 12)      (SEQ. ID. NO.: 13)
GIYIINL                 DHQPLTEASYVNLPTIALCNTD
(SEQ. ID. NO.: 14)      (SEQ. ID. NO.: 15)
KLLLAARAIVAIE           GVQVPSVPIQQF
(SEQ. ID. NO.: 16)      (SEQ. ID. NO.: 17)
PADVSVISS
(SEQ. ID. NO.: 18)
ATPIAGR
(SEQ. ID. NO.: 19)
PLRYVDIAIPC             FREPRLLVVTDPR
(SEQ. ID. NO.: 20)      (SEQ. ID. NO.: 6)
AHSVGL                  VVTDRADHQPLT
(SEQ. ID. NO.: 21)      (SEQ. ID. NO.: 22)
MPDLYFYR                VVTDPRADHQP
(SEQ. ID. NO.: 23)      (SEQ. ID. NO.: 24)
APEFTAAQPEVA
(SEQ. ID. NO.: 25)

Actual Used

FREPRLLVVTDPR
(SEQ. ID. NO.: 6)
VTDPRADHQPLTE
(SEQ. ID. NO.: 3)
YRDPEEIEKEEQ
(SEQ. ID. NO.: 4)
FPTEDWSAQPATED
(SEQ. ID. NO.: 5)

For Conjugation:

FREPRLLVVTDPRC
(SEQ. ID. NO.: 8)
CVTDPRADHQPLTE
(SEQ. ID. NO.: 26)
YRDPEEIEKEEQC
(SEQ. ID. NO.: 9)
CFPTEDWSAQPATED
(SEQ. ID. NO.: 27)

Previously Published Epitopes

TEDWSA
(SEQ. ID. NO.: 28)
TPGTFNQIQAAFREPRLLV
(SEQ. ID. NO.: 29)
SGALDVLQ
(SEQ. ID. NO.: 30)
AAGTHLGGTNLDFQMEQYIY
(SEQ. ID. NO.: 31)

TABLE 1-continued

| List of different putative epitopes for antibody generation<br>Possible Antigenic Regions for Development of OFA/iLRP antibodies |
|---|
| DGIYIINLKRTWEKLLLAAR<br>(SEQ. ID. NO.: 32) |
| AIVAIENPADVSVISSRNTG<br>(SEQ. ID. NO.: 33) |
| QRAVLKFAAATGATPIAGRF<br>(SEQ. ID. NO.: 34) |
| TPGTFTNQIQAAFREPRLLV<br>(SEQ. ID. NO.: 35) |
| ALCNTDSPLAYVDIAIPCNN<br>(SEQ. ID. NO.: 36) |
| IPCNNKGAHSVGLMWWMLAR<br>(SEQ. ID. NO.: 37) |
| AAAEKAVTKEEFQGEWTAPA<br>(SEQ. ID. NO.: 38) |
| QFPTEDWSAQPATEDWSAAP<br>(SEQ. ID. NO.: 39) |

TABLE 2

| Immunizing peptides designed against OFA/iLRP antibodies | |
|---|---|
| Peptide 1 | FFREPRLLVVTDPRC<br>(SEQ. ID. NO.: 40) |
| Peptide 2 | CVTDPRADHQPLTE<br>(SEQ. ID. NO.: 26) |
| Peptide 3 | YRDPEEIEKEEQC<br>(SEQ. ID. NO.: 9) |
| Peptide 4 | CFPTEDWSAQPATED<br>(SEQ. ID. NO.: 27) |

What is claimed is:

1. An isolated antibody or a fragment thereof that specifically binds to an epitope of the oncofetal antigen/immature laminin receptor protein (OFA/iLRP), wherein the epitope is or lies within the amino acid sequence of VTDPRADHQPLTE (SEQ ID NO.:3), YRDPEEIEKEEQ (SEQ ID NO.:4), or YRDPEEIEKEEQC (SEQ ID NO.:9).

2. The isolated antibody of claim 1, wherein the epitope is or lies within the amino acid sequence of VTDPRADHQPLTE (SEQ ID NO.:3), or YRDPEEIEKEEQ (SEQ ID NO.:4).

3. The isolated antibody of claim 1, wherein the antibody is a monoclonal antibody.

4. The isolated antibody of claim 3, wherein the epitope is or lies within the amino acid sequence of YRDPEEIEKEEQC (SEQ ID NO.:9).

5. A pharmaceutical composition comprising the antibody of claim 1.

6. The composition of claim 5, wherein the antibody is a monoclonal antibody.

7. The composition of claim 5, further comprising a pharmaceutically acceptable carrier.

8. The isolated antibody of claim 1, which is conjugated to a detectable label.

9. The isolated antibody of claim 8, wherein the detectable label is selected from the group consisting of radioisotopes, fluorescent labels, and enzyme-substrate labels.

10. A pharmaceutical composition of claim 7, wherein the pharmaceutically acceptable carrier comprises a stabilizing agent, a wetting agent, an emulsifying agent, a salt, an encapsulating agent, a buffer, a skin penetration enhancing agent, or a combination of two or more thereof.

11. The pharmaceutical composition of claim 7, wherein the carrier comprises a sterile diluent, an antioxidant, a chelating agent, a buffer, an agent for the adjustment of tonicity, a pH adjusting agent, or a combination of two or more thereof.

12. The pharmaceutical composition of claim 7, wherein the carrier comprises physiological saline, sterile water, Cremophor EL, or phosphate buffered saline.

13. The pharmaceutical composition of claim 7, wherein the carrier comprises an agent that delays absorption, a preservative, or both.

14. The pharmaceutical composition of claim 5, which is formulated in a controlled release formulation.

15. The pharmaceutical composition of claim 14, wherein the antibody is contained in a microencapsulated delivery system.

16. The pharmaceutical composition of claim 14, wherein the antibody is encapsulated in a liposome.

17. The pharmaceutical composition of claim 4, which is formulated for oral administration.

18. The pharmaceutical composition of claim 4, which is formulated for parenteral administration.

19. The pharmaceutical composition of claim 4, which is formulated as a dosage unit form.

* * * * *